(12) United States Patent
Zasloff et al.

(10) Patent No.: US 6,596,712 B2
(45) Date of Patent: Jul. 22, 2003

(54) TREATMENT OF CARCINOMAS USING SQUALAMINE IN COMBINATION WITH OTHER ANTI-CANCER AGENTS OR MODALITIES

(75) Inventors: Michael Zasloff, Merion Station, PA (US); Jon Williams, Robbinsville, NJ (US); Mitchell H. Sokoloff, Charlottesville, VA (US)

(73) Assignee: Genaera Corporation, Plymouth Meeting, PA (US)

( * ) Notice: Subject to any disclaimer, the term of this patent is extended or adjusted under 35 U.S.C. 154(b) by 0 days.

(21) Appl. No.: 09/803,740

(22) Filed: Mar. 12, 2001

(65) Prior Publication Data

US 2001/0046521 A1 Nov. 29, 2001

Related U.S. Application Data

(63) Continuation of application No. PCT/US99/20645, filed on Sep. 10, 1999, which is a continuation-in-part of application No. 09/150,724, filed on Sep. 10, 1998, which is a continuation-in-part of application No. 08/840,706, filed on Apr. 25, 1997, now Pat. No. 6,147,060.
(60) Provisional application No. 60/016,387, filed on Apr. 26, 1996.

(51) Int. Cl.$^7$ .............................................. A61K 31/56
(52) U.S. Cl. ........................................ 514/171; 514/182
(58) Field of Search .................................. 514/182, 171

(56) References Cited

U.S. PATENT DOCUMENTS

| | | | |
|---|---|---|---|
| 3,016,390 A | 1/1962 | Counsell ................. | 260/397.5 |
| 3,370,070 A | 2/1968 | Klimstra et al. ........ | 260/397.5 |
| 4,220,598 A | 9/1980 | Hixson, Jr. et al. ...... | 260/397.1 |
| 4,372,888 A | 2/1983 | Hjelmeland .............. | 260/397.1 |
| 4,425,273 A | 1/1984 | Iida et al. ................. | 260/397.1 |
| 4,514,393 A | 4/1985 | Castagnola et al. ...... | 260/397.1 |
| 4,545,938 A | 10/1985 | Mosbach et al. ........ | 260/371.1 |
| 4,550,163 A | 10/1985 | Voss et al. .................. | 544/244 |
| 4,565,811 A | 1/1986 | Di Schiena ................ | 544/182 |
| 4,771,042 A | 9/1988 | Braughler et al. .......... | 514/171 |
| 4,793,948 A | 12/1988 | Hatono et al. ............ | 260/397.1 |
| 4,966,897 A | 10/1990 | Angelastro et al. ......... | 514/177 |
| 4,994,443 A | 2/1991 | Folkman et al. ............ | 514/177 |
| 5,001,116 A | 3/1991 | Folkman et al. ............ | 514/177 |
| 5,004,737 A | 4/1991 | Kim et al. ................... | 514/177 |
| 5,039,529 A | 8/1991 | Bergendal et al. ............ | 514/56 |
| 5,057,509 A | 10/1991 | Pellicciari et al. .......... | 514/182 |
| 5,061,701 A | 10/1991 | Pellicciari et al. .......... | 514/180 |
| 5,063,222 A | 11/1991 | Komoto et al. ............. | 514/180 |
| 5,075,464 A | 12/1991 | Blohm et al. ................ | 514/177 |
| 5,135,919 A | 8/1992 | Folkman et al. .............. | 514/56 |
| 5,192,756 A | 3/1993 | Zasloff et al. ............... | 514/182 |
| 5,250,524 A | 10/1993 | Kramer et al. ............... | 514/177 |
| 5,436,026 A | 7/1995 | Berta ........................ | 427/2.14 |
| 5,637,691 A | 6/1997 | Frye et al. ................... | 540/106 |
| 5,721,226 A | 2/1998 | Frye et al. ................... | 514/169 |
| 5,792,635 A | 8/1998 | Zasloff ....................... | 435/184 |
| 5,856,535 A | 1/1999 | Zasloff et al. ............... | 522/521 |

FOREIGN PATENT DOCUMENTS

| | | |
|---|---|---|
| EP | 0 394 971 A1 | 10/1990 |
| EP | 0 466 315 A2 | 1/1992 |
| FR | 2 361 899 | 3/1978 |
| GB | 1 565 351 | 4/1980 |
| WO | WO87/02367 | 4/1987 |
| WO | WO91/19731 | 12/1991 |
| WO | WO93/25197 | 12/1993 |
| WO | WO94/19366 | 9/1994 |
| WO | WO94/20520 | 9/1994 |
| WO | WO95/24415 | 9/1995 |
| WO | WO96/40151 | 12/1996 |
| WO | WO96/40728 | 12/1996 |

OTHER PUBLICATIONS

McKenna, James et al., "Bis–steroids as Potential Enzyme Models: Perylene Solubilisation and Dye Spectral Changes with Aqueous Solutions of Some Derivatives of Conessine and Cholic Acid:" *J.C.S. Chem. Comm.,* 1977, pp. 809–811.

Crum, Rosa et al., "A Class of Steroids Angiogenesis in the Presence of Heparin or a Heparin Fragment," Science, vol. 230, 1985, pp. 1375–1378.

Derwent Abstract No. 86–085704, "Anticancer Drug Contains Shark Liver Extract Doxorubicin," 1984.

Biosis No. 82085007, "Studies on Antitumor Activity of Squalene and Its Related Compounds," Yakugaku Zasshi, 1986.

(List continued on next page.)

*Primary Examiner*—Jerome D. Goldberg
(74) *Attorney, Agent, or Firm*—Morgan, Lewis & Bockius LLP

(57) ABSTRACT

A method for treating a tumor includes a first treatment procedure using a conventional cancer treatment technique, and a second treatment procedure which includes administering an effective amount of squalamine. Synergistically effective amounts are preferred. The first treatment procedure may be a treatment with one or more conventional cytotoxic chemical compounds. As examples, the cytotoxic chemical compound may be a nitrosourea (such as BCNU), cyclophosphamide, doxorubicin, 5-fluorouracil, paclitaxel and its derivatives, cisplatin or other platinum containing cancer treating agents. Alternatively, the first treatment may be a treatment with one or more conventional anti-hormonal agents. As examples, the anti-hormonal agents may be a LHRH (luteinizing hormone releasing hormone) agonist or an anti-androgen such as flutamide, biclutamide, nilutamide, and luprolide. These conventional cancer treatments compounds and the squalamine may be administered by any suitable route. The first treatment procedure may take place prior to the second treatment procedure, after the second treatment procedure, or the two treatment procedures may take place simultaneously. As an alternative, the first treatment procedure may be a conventional radiation treatment regimen. As a further alternative the first treatment procedure may be a combination of treatment with one or more conventional cytotoxic chemical compounds and a conventional radiation treatment regimen.

14 Claims, 17 Drawing Sheets

OTHER PUBLICATIONS

Chemical Abstract No. 111: 17264, "Increasing the Therapeutic Efficacy of Antitumor Drugs," 1989.

Ikekawa, T., et al., Biosis No. 82085007, "Studies on Antitumor Activity of Squalene and Its Related Compounds," *Yakugaku Zasshi* (1986).

Konovalova, V.P., et al., Chemical Abstract No. 111(3):17264, "Increasing the Therapeutic Efficacy of Antitumor Drugs" (1989).

Bellini, A.M. et al., "Antimicrobial Activity of Basic Cholane Derivatives, Part IX." Arch. Pharm. (Weinheim) 323,201–205 (1990).

Bellini, Anna M. et al., Antimicrobial Activity of Basic Cholane Derivatives. Part X. Synthesis of 3α–and 3β–amino–5β–amino–cholan–24–oic Acids, *Steroids,* vol. 56, Jul. 1991, pp. 395–397.

Gagliardi, A., et al., "Inhibition of Angiogenesis by Antiestrogens," *Cancer Research,* 53, pp. 533–535, Feb. 1, 1993.

Moore, Karen S. et al., "Squalamine : An Aminosterol Antibiotic from the Shark," *Proc. Natl. Acad. Sci., USA,* vol. 90, pp. 1354–1358, Feb. 1993.

Wehrli, S. et al., "Structure of the Novel Steroidal Antibiotic Squalamine Determined by Two–Dimentional NMR Spectroscopy," *Steroids,* vol. 58, No. 8, Aug. 1993, pp. 370–378.

Zasloff, M., et al., Children's Hospital of Pennsylvania, "Aminosterol Antibiotic." Current Opinion in Therapeutic Patents Sep. 1993, pp. 1369–1370.

Moriarty, Robert M. et al. "Synthesis of Squalamine, A Steroidal Antibiotic from the Shark," *Tetrahedron Letters,* vol. 35, No. 44, pp. 8103–8106, 1994.

Sadownik, Andrzej et al. "Rapid Construction of a Squalamine Mimic:" *J. A. Chem. Soc.,* 1995, vol. 117, pp. 6138–6139.

Marshall, J., "Shark Cartilage for Cancer Treatment," *P&T Newsletter,* Mar. 1996, pp. 159–160.

Bavinaga, M., "Designing Therapies that Target Tumor Blood Vessels:" *Science,* vol. 275, Jan. 24, 1997, pp. 482–484.

Akhter, "Squalamine, A Novel Aminosterol Antibiotic is a Specific Inhibitor of Epithelial Brush Border NA+/H+ Exchanger Isoform, NHE3," *FASEB Journal,* vol. 10, No. 3 (1996), p. A89.

Nath, "The Novel Aminoesterol Antibiotics Squalamine and 1436 are Specific Inhibitors of Epithelial Brush Border NA+/H+ Exchanger (NHE) Isoform, NHE3," *Gastroenterology,* vol. 110, No. 4, Suppl. (1996), A349.

Bissery, M., et al., "Preclinical Profile of Docetaxel (Taxotere): Efficacy as a Single Agent and in Combination," *Seminars in Oncology,* 22(6):3–16 (1995).

Kobayashi, E., et al., "Characteristics of Antitumor Activity of KW–2189, a Novel Water–soluble Derivative of Duocarmycin, against Murine and Human Tumors," *Cancer Research* 54(9):2404–2410 (1994).

Kubota, T., et al., Antitumor Effect and Metabolic Activation of Cyclophosphamide and 4–Hydroperoxycyclophosphamide in the Human Breast Carcinoma(MX–1)–Nude Mouse System, *GANN: Japanese Journal of Cancer Research* 74:437–444 (1983).

Teicher, B., "Angiogenesis and Cancer Metastases: Therapeutic Approaches," *Critical Reviews in Oncology/Hematology* 20:9–39 (1995).

Tse, M., et al., "The Mammalian Na/HExchanger Gene Family—Initial Structure/Function Studies," *Journal of the American Society of Nephrology,* 4(4):969–975 (1993).

Wiemann, M., et al., "Pharmacology of Antineoplastic Agents," *Medical Oncology: Basic Principles and Clinical Management of Cancer,* (New York: MacMillan Publishing Co.), p. 292–362 (1985).

Boring, C.C. et al., "Cancer Statistics, 1994," *CA: Cancer J. Clin.,* 44(1):7–26 I(1994).

| CHEMOTHERAPEUTIC AGENT | NO SQUALAMINE | 20 MG/KG/DAY SQUALAMINE (SUBCUTANEOUS) |
|---|---|---|
| ---- | 36 (CONTROL) | 11 |
| CYCLOPHOSPHAMIDE | 7 | 1.5 |
| CISPLATIN | 16.5 | 4.5 |

TREATMENT OF CARCINOMAS USING SQUALAMINE IN COMBINATION WITH OTHER ANTI-CANCER AGENTS OR MODALITIES

This application is a continuation of copending International Application No. PCT/US99/20645 filed Sep. 10, 1999, which is a continuation-in-part of application Ser. No. 09/150,724, filed Sep. 10, 1998, which is a continuation-in-part of 08/840,706, filed Apr. 25, 1997, now U.S. Pat. No. 6,147,060 which claims the benefit of provisional application No. 60/016,387, filed Apr. 26, 1996, under 35 U.S.C. §119. All of these applications are herein incorporated by reference in their entirety.

BACKGROUND OF THE INVENTION

I. Information Relating to Previous Squalamine Applications

This invention relates to various methods for using squalamine. Squalamine, having the structure illustrated in FIG. 1, is an aminosterol which has been isolated from the liver of the dogfish shark, Squalus acanthias. This aminosterol is the subject of U.S. Pat. No. 5,192,756 to Zasloff, et al., which patent is entirely incorporated herein by reference. Methods for synthesizing squalamine have been devised, such as the methods described in WO 94/19366 (published Sep. 1, 1994). This PCT publication is entirely incorporated herein by reference. This PCT application also relates to U.S. patent Appln. Ser. No. 08/023,347 (filed Feb. 26, 1993), which application also is entirely incorporated herein by reference. Additional methods for synthesizing squalamine also are described in U.S. patent Appln. Ser. No. 08/985,876 filed Dec. 5, 1997, which application also is entirely incorporated herein by reference.

U.S. Pat. Nos. 5,733,899 and 5,721,226 describe the use of squalamine as an antiangiogenic agent. These U.S. patents are entirely incorporated herein by reference. Additional uses of squalamine (e.g., as a sodium/proton exchanger (isoform 3), or NHE3, inhibiting agent and as an agent for inhibiting the growth of endothelial cells) and squalamine synthesis techniques are disclosed in U.S. Pat. No. 5,792,635. This U.S. patent is also entirely incorporated herein by reference.

II. Information Relating to this Invention

About 50,000 new cases of CNS (central nervous system) tumors are diagnosed each year. Of these, about 35,000 are metastatic tumors (e.g., lung, breast, melanomas) and about 15,000 are primary tumors (mostly astrocytomas). Astrocytomas, along with other malignant gliomas (i.e., cancers of the brain), are the third leading cause of death from cancer in persons between the ages of 15 and 34.

Treatment options for a patient with a CNS tumor are very limited. Currently, surgery is the treatment of choice. Surgery provides a definite diagnosis, relieves the mass bulkiness of the tumor, and extends survival of the patient. The only post-surgery adjuvant treatment which is known to work on CNS tumors is radiation, and it can prolong survival. Radiation treatment, however, has many undesirable side effects. It can damage the normal tissue of the patient, including the brain tissue. Radiation also can cause the patient to be sick (e.g., nausea) and/or to temporarily lose their hair.

The other common post-surgery adjuvant cancer treatment, chemotherapy, is relatively ineffective against CNS tumors. Specifically, chemotherapy against CNS tumors with nitrosoureas is not curative. Many other cancer treating agents have been studied and tested, but generally they have a minimal effect on extending survival.

In view of these limited treatment options, the current prognosis for persons with CNS tumors is not good. The median survival term for patients with malignant astrocytomas having surgery and no adjuvant treatment is about 14 weeks. Radiation therapy after surgery extends the median to about 36 weeks. The current two year survival rate for all forms of treatment is less than 10%.

To maximize survival, it is critical to begin treatment in the early stages of CNS tumor development. Typically, the extent of tumor angiogenesis (i.e., blood vessel formation) correlates with survival in the patient. CNS tumors are among the most angiogenic of all human tumors. When the tumor is small, however, it is in an "avascular" phase, and its growth is restricted by a diffusion mechanism (i.e., the cells receive their nutrition, etc. by diffusion into the cell). In this phase, the tumor is viable, but not growing, and it is unable to spread. Over time, however, angiogenesis begins and the tumor converts to a "vascular" phase. In this phase, perfusion replaces diffusion as the growth mechanism, and tumor growth is exponential (i.e., the tumor has its own blood vessels to provide nutrients, etc.). Mitotic cells cluster around new blood vessels and metastases occur in the vascular phase (i.e., the tumor can spread to other areas in the body). Therefore, by treating the tumor early (before it reaches the vascular phase), one can hope to inhibit metastatic spread as well as control the primary tumor.

Other types of cancer also are difficult to combat by known cancer treatments. Lung cancer kills more Americans annually than the next four most frequently diagnosed neoplasms combined. Estimates for 1994 indicate more than 170,000 new cases of lung cancer and approximately 150,000 deaths (Boring et al.; CA Cancer J. Clin. 1994, 44: 7–26). Approximately 80% of primary lung tumors are of the non-small cell variety, which includes squamous cell and large cell carcinomas, as well as adenocarcinomas.

Single-modality therapy is considered appropriate for most cases of early and late stage non-small cell lung cancer (NSCLC). Early stage tumors are potentially curable with surgery, chemotherapy, or radiotherapy, and late stage patients usually receive chemotherapy or best supportive care. Intermediate stage or locally advanced NSCLC, which comprises 25% to 30% of all cases of NSCLC, is more typically treated with multimodality therapy. This is a stage of tumor development when angiogenesis is a very important factor. New blood vessels are needed to support further tumor growth and for the development of metastases. Therefore, this stage is amenable to treatment with antiangiogenic agents to prevent the development of new blood vessels. The efficacy of this therapy can be further improved by the combination of the antiangiogenic therapy with cytotoxic chemotherapy or radiation therapy to eliminate existing tumor.

Breast cancer also presents treatment difficulties using known agents. The incidence of breast cancer in the United States has been rising at a rate of about 2%/year since 1980, and the American Cancer Society estimated that 182,000 cases of invasive breast cancer were diagnosed in 1995. Breast cancer is usually treated with surgery, radiotherapy, chemotherapy, hormone therapy, or combinations of the various methods. Like other solid tumors, breast cancer requires the development of new blood vessels to support its growth beyond a certain size, and at that stage in its development, it will be amenable to treatment with antiangiogenic agents.

A major reason for the failure of cancer chemotherapy in breast cancer is the development of resistance to the cytotoxic drugs. Combination therapy using drugs with different mechanisms of action is an accepted method of treatment which prevents development of resistance by the treated tumor. Antiangiogenic agents are particularly useful in combination therapy because they are not likely to cause resistance development since they do not act on the tumor, but on normal host tissue.

Prostate cancer is another cancer for which new therapies are needed. Despite the prevalence of prostate cancer as the most frequently diagnosed malignancy among American men, mechanisms of prostate carcinogenesis are poorly understood. The multiplicity of factors involved in the development, proliferation, and dissemination of human prostate cancer, as well as their relationships and interaction with one another, magnify the difficulty of treatment.

Both prostate tumor cell growth and metastasis require adequate metabolic support as well as vascular access and thus rely on angiogeneis. The prostate cancer cell-extracellular matrix (ECM)/stromal relationship is also significant to the growth and spread of human prostate cancer. Of the numerous growth factors present in the ECM, b-FGF (basic fibroblast growth factor, also known as FGF-2) and VEGF (vascular endothelial growth factor) stand out as having been implicated in both inducing a malignant phenotype and in promoting and maintaining angiogenic processes. Ultimately, the outcome of a patient with prostate cancer largely depends upon the tumor's capacity for unhindered growth, local invasion, and the establishment of distant metastasis. Thus, anti-angiogenic agents may effectively inhibit the growth and metastasis of such tumors.

Current therapies for prostate cancer focus on inhibiting the androgen agent. Radiation is, as with many cancers, an initial line of treatment, often followed by hormonal therapy. Such hormonal therapy seeks to specifically inhibit the androgen agent. Inhibition can result from either surgical castration or chemical castration with agents such as LHRH (luteinizing hormone releasing hormone) agonists and anti-androgens (such as flutamide, biclutamide, nilutamide, and luprolide). However, these therapies fail in most patients who thereafter present with hormone-refractory lesions. Currently, few therapeutic options exist for men with hormone-refractory prostate cancer, and none offer much durability. At this point, tumor growth can be so accelerated that life expectancy rarely exceeds six months to one year. Indeed, 70% of these patients will eventually die of their hormonal refractory disease.

In such patients, who have undergone anti-hormone therapies, the remaining prostate tumor cells are likely undergoing rejuvenated proliferation. Accordingly, anti-angiogenic agents may be most effective at this stage, particularly agents that are most potent on freshly sprouting, young blood vessels, thereby preventing neovascularity and repressing further tumor growth and metastasis.

Ovarian cancer is the most serious gynecologic tumor type. Over 50% of all cancer-related gynecologic deaths are attributable to ovarian cancers, of which 80–90% are epithelial-derived tumors. In 1997 there were 26,700 new cases of ovarian cancer and more than 14,000 deaths. There is a clear genetic component to ovarian cancer. Newly developed detection methods have shown strong correlations between breast cancer, ovarian cancer and expression of genetic markers that include BRCA1 or mutant oncogenes such as aberrant forms of erbB-2 or c-Myc. Another good marker for ovarian cancer of clinical utility is the circulating analyte CA125, for which serum levels generally reflect the state of cancer progression. CA125 is often monitored in ovarian cancer, although it is not a validated marker. There is also a hormonal influence on cancer risk in ovarian cancer, as is seen in breast cancer About one-third of ovarian cancer patients present with localized disease. Early stage ovarian cancer is treatable with some combination of surgery, radiation and chemotherapy; the 5 year survival rate for localized ovarian cancer is greater than 80%. However, the 5 year survival rate for metastatic stage III or IV ovarian cancer is less than 20%. It is these advanced patients, those for whom the ovarian tumors escape the ovarian capsule and invade intraperitoneal surfaces, who require the most aggressive therapy yet benefit only marginally with chemotherapy. The first line chemotherapeutic treatment for ovarian cancers has been the use of platinum-based regimens for over a decade. With the advent of newer agents such as the taxanes (paclitaxel, docetaxel), gemcitabine, newer vinca alkaloids (vinorelbine), and topoisomerase inhibitors (topotecan, irinotecan), combination chemotherapy has become more widely explored in advanced ovarian cancer patients. The combination (sequential or concurrent) of a taxane and a platinum agent is the present standard first line treatment for advanced ovarian cancer patients. However, the poor prognosis for these patients despite the aggressive use of chemotherapy and surgery (with or without radiotherapy) suggests the further addition of non-cytotoxic agents such as an angiogenesis inhibitor would be beneficial.

There are recent estimates that the incidence of deaths due to liver cancer worldwide could be as high as $10^6$ or more per year. Hepatocellular carcinoma (HCC) or hepatoma is the most common liver cancer tumor and is a tumor type that is closely associated with chronic hepatitis B or hepatitis C infection. The high frequency of hepatitis viral infections observed in Asia and Africa make these regions the sites of the largest number of liver cancers, most of which are HCC tumors. Although viral infection is considered essential for predisposition to HCC, infection alone is not the only contributing factor to hepatocellular transformation and proliferation. By comparison, there were 13,500 deaths of liver cancer in 1992 in the United States, of which two-thirds were HCC.

The prognosis for liver cancers is universally poor with the minor exception of those tumors which are only locally invasive and are located favorably for curative surgical removal. For locally advanced disease, limited efficacy has been seen with interferon therapy, polyprenoic acid (vitamin A derivative), 5-fluorouracil or cryoablation. No meaningful combination chemotherapy has proven itself in human trials for HCC to date, but the urgent clinical need continues to drive experimental evaluation of various therapeutic approaches. A recent report (LX Qin et al., *Ann Acad Med Singapore* 28,147–51 (1999)) suggests that angiogenesis inhibitors can inhibit hepatoma tumor growth in mouse xenograft tumor models and may be candidates for the control of recurrence and metastasis after HCC resection. It therefore is a reasonable approach to consider combining treatment of HCC patients not eligible for curative surgery with an angiogenesis inhibitor and an active second modality such as α-interferon, a cytotoxic agent such at 5-fluorouracil, or a vitamin A derivative.

Pediatric tumors are among the less common tumors seen in the oncology clinic. There were only 7700 children under the age of 15 reported with cancer in 1994. Although this only represents about 1% of the entire cancer population, much attention is given by oncologists to the special problems and to the social benefit associated with treating cancer among children. The most common solid tumor among affected children is neuroblastoma, which is of neuroendocrine origin.Other solid tumors among children are Wilms' tumor, rhabdomyosarcoma and retinoblastoma. Neuroblastomas represent 9% of all childhood cancers, but 15% of pediatric cancer deaths. Many pediatric tumors have a genetic basis; for example, it is estimated that perhaps 20% of neuroblastomas are genetic in nature.

Neuroblastomas most commonly are seen in the abdomen, many of these being found in the adrenal gland. The median age at diagnosis for neuroblastoma patients is 2 years. Surgery can be curative in early stage neuroblastomas, but most children present with metastatic disease. Even in children with minimal residual disease following surgery, recurrences are seen in more than half of all patients. Clinical trials have emphasized the positive value of using post-surgical chemotherapy with or without radiation therapy. Neoadjuvant chemotherapy is also commonly used with neuroblastoma patients, but it is more common to use chemotherapy in the adjuvant setting. Neuroblastoma is a particularly difficult tumor to treat, and platinum-based regimens are frequently used in first or second-line treatments. The chemotherapeutic regimens for pediatric patients are highly aggressive, often involving megatherapy with 4–6 cytotoxic agents. Neuroblastoma tumors represent an interesting opportunity for antiangiogenic therapy as neuroblastomas are highly vascular, grow quickly and metastasize rapidly. Antiangiogenic therapy for neuroblastoma may allow new aggressive combination chemotherapy treatments involving cytostatic agents since they are anticipated to provide minimal additional toxic side effects and should not diminish the efficacy of the cytotoxic agents to which they are matched.

SUMMARY OF THE INVENTION

It is an object of this invention to provide a method for treating malignant and cancerous tumors using squalamine, in combination with other, conventional cancer treating agents. Although the invention can be applied to any responsive tumor, in particularly preferred aspects of the invention, the tumors treated are found in the CNS, lung, breast, ovary, liver, neuroendocrine and prostate tissues.

In one method according to the invention, squalamine is used in combination with conventional cancer treatments to treat tumors. Such conventional cancer treatments include the use of cytotoxic agents as well as anti-hormonal agents. In one embodiment, the tumor is treated by administering an effective amount of a cytotoxic chemical compound or a combination of cytotoxic compounds in a first treatment procedure, and an effective amount of squalamine is administered in a second treatment procedure.

In this method, the cytotoxic chemical compound used in the first treatment procedure is a conventional cancer treating agent. Preferable agents include a nitrosourea, cyclophosphamide, doxorubicin, epirubicin, 5-fluorouracil, topotecan and irinotecan, carmustine, estramustine, paclitaxel and its derivatives, and cisplatin, carboplatin, iproplatin and related platinum compounds. These conventional cancer treating agents are well known to those skilled in this art. Note, M. C. Wiemann and Paul Calabresi, "Pharnacology of Antineoplastic Agents," *Medical Oncology*, Chapter 10, edited by Paul Calabresi, et. al., McMillan Publishing (1985). *Medical Oncology* is entirely incorporated herein by reference. One particularly preferred nitrosourea is BCNU, which also is known as carmustine. Another preferred cytotoxic agent is a platinum compound such as carboplatin, iproplatin or cisplatin, and yet another is cyclophosphamide. Other conventional cytotoxic chemical compounds, such as those disclosed in *Medical Oncology*, supra., can be used without departing from the invention.

In another embodiment the tumor is treated by first inhibiting hormones that affect the tumor and then administering an effective amount of squalamine in a second treatment procedure. In one aspect, the hormones may be specifically inhibited. When the tumor is of the prostate, the hormone inhibition may result from orchiectomy, i.e., the removal of one or both testes. Orchiectomy may result from surgery or from the administration of chemical agents such as LHRH (luteinizing hormone releasing hormone) agonists and/or anti-androgens (such as flutamide, biclutamide, nilutamide or luprolide).

The cytotoxic and anti-hormonal chemical compounds administered in the first treatment step may be administered by any conventional technique used in the art (i.e., oral, subcutaneously, intralymphatically, intraperitoneally, intravenously, or intramuscularly). In one embodiment of the invention, the cytotoxic chemical compound (preferably BCNU, cisplatin, or cyclophosphamide) is administered intravenously. Likewise, squalamine can be administered by any conventional administration method known in the art, such as those mentioned above. Subcutaneous injections of squalamine one or two times a day are used in one embodiment of this invention. Intravenous administration of squalamine one or two times a day are used in another embodiment of the present invention.

The first treatment procedure with the cytotoxic chemical or anti-hormonal compound may take place prior to the second treatment procedure (using squalamine), after the second treatment procedure, or at the same time as the second treatment procedure. Furthermore, the first treatment procedure may be completed before the second treatment procedure is initiated (or vice versa). In one embodiment of the invention, the first treatment procedure is a one time intravenous administration of a cytotoxic chemical or anti-hormonal compound (i.e., BCNU, cisplatin, or cyclophosphamide), and the second treatment procedure involves daily subcutaneous injections of squalamine.

In addition, the invention encompasses the use of squalamine together with cytotoxic compounds or antihormonal compounds or the use of two or more of these compounds with squalamine. The invention also encompasses the use of squalamine together with a cytostatic agent or the use of these two treatment modalities with a cytotoxic compound. A cytostatic agent is any chemical compound which is capable of arresting the growth of tumor cells or normal stromal cells in a tumor but which is not toxic at pharmacologically active concentrations. A pharmacologically active concentration of a cytostatic agent used in the first treatment procedure may be any know cell growth modulator, but it is preferably the calcium pump inhibitor carboxyamidotriazole.

In a second method for treating a tumor according to the invention, the first treatment procedure is a radiation treatment, which may be one or more conventional radiation modalities, using a conventional radiation treatment regimen known to those skilled in the art. The tumor is exposed to radiation in this first treatment procedure. In a second treatment procedure, an effective amount of squalamine is administered to treat the tumor. Appropriate timing of the radiation treatment procedure with respect to the squalamine treatment regimen can be determined by those skilled in the art through routine experimentation in order to provide effective tumor treatment.

In addition to radiation and squalamine treatments, the tumor also may be treated with one or more cytoxic chemical or anti-hormonal compounds in a third treatment procedure. Further, in addition to radiation and squalamine treatments, the tumor also may be treated with one or more cytostatic chemical compounds in a third treatment procedure. The cytostatic agent used in the third threatment procedure may be any known cell growth modulator which is not cytotoxic, but it is preferably the calcium pump inhibitor carboxymidotriazole. It is additionally envisioned in the present embodiment of the invention that tumors treated with radiation, squalamine and a cell growth modulator may also be treated with one or more cytotoxic chemical compounds in a fourth treatment procedure.

Of course, the invention also relates to the use of both cytotoxic chemical and/or anti-hormonal compounds in addition to radiation, or any other combination of treatment methods.

BRIEF DESCRIPTION OF THE DRAWINGS

These and other advantageous features of the invention will be more fully appreciated when considered based on the following detailed description and the attached drawings, wherein:

FIG. 13 illustrates the number of lung metastases following various chemotherapeutic treatment procedures in mice with subcutaneous implanted Lewis lung carcinomas.

FIG. 14b illustrates the effects of squalamine, VEGF, and a combination of VEGF and squalamine treatment an C4-2 human prostate cell growth. In both situations, [$^3$H]-thymidine incorporation assays were utilized.

DETAILED DESCRIPTION OF THE INVENTION

Figure 1:
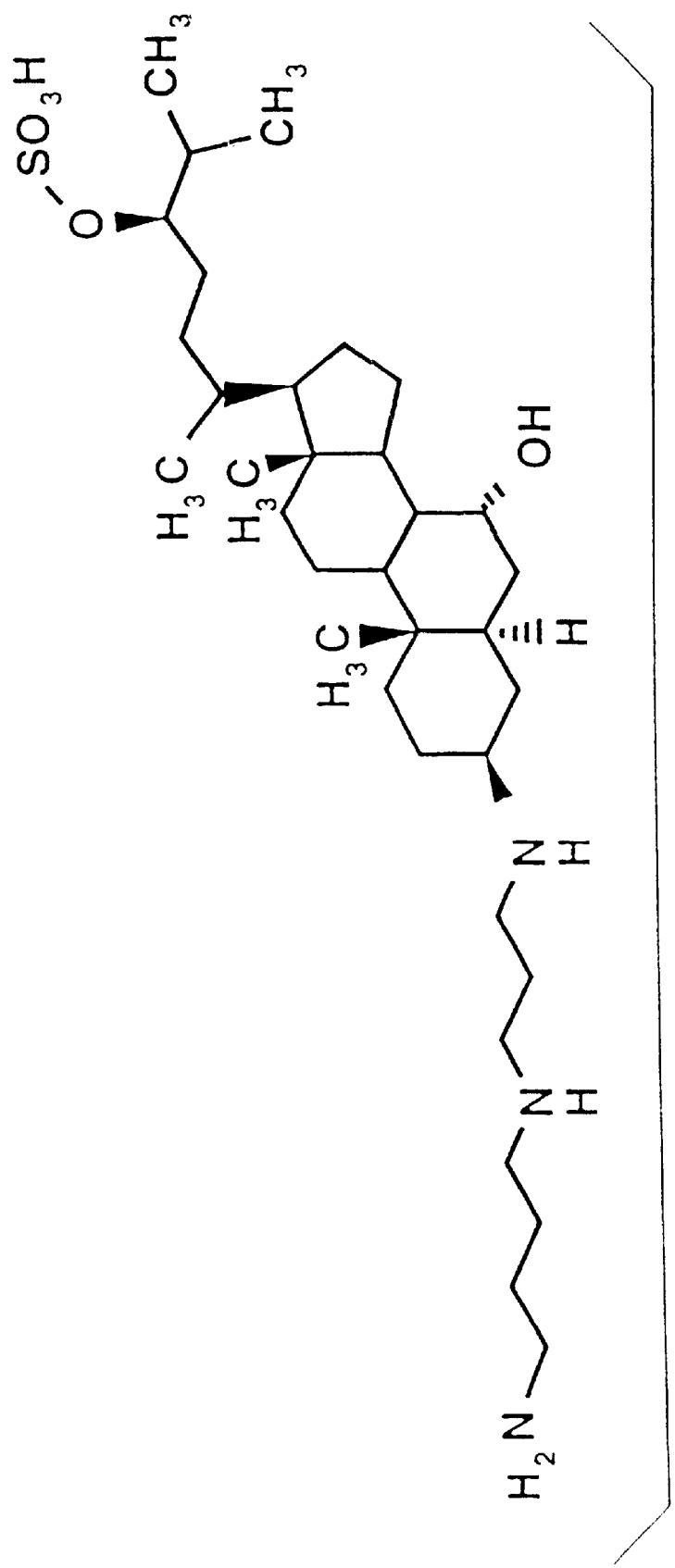
FIG. 1 shows the general structural formula of squalamine.

Squalamine has been recognized to have angiogenesis inhibiting activity, i.e., it inhibits the formation of blood vessels. Therefore, it is believed that squalamine, as an antiangiogenic agent, will be effective in treating certain diseases or ailments which depend on neovascularization. For example, squalamine may be used for treating such disparate conditions as solid tumor cancers, macular degeneration, diabetic retinopathy, psoriasis, or rheumatoid arthritis, all of which require a separate and new blood flow.

In addition, squalamine can selectively inhibit certain sodium/proton exchangers (also called "NHEs" or "proton pumps" in this application). Several different isoforms of NHE are known to exist in mammals (i.e., NHE1, NHE2, NHE3, NHE4, and NHE5). Squalamine has been found to specifically inhibit NHE3 and not NHE1 or NHE2. Accordingly, squalamine may be used for treating proliferation or activation dependent conditions which rely on the function of NHE3, such as cancer, viral diseases, and ischemic reprofusion injury.

Further studies with squalamine and NHE have demonstrated that squalamine acts on a very specific portion of the NHE3, namely the 76 carboxyl-terminal amino acids of the molecule. If this portion of the NHE3 molecule is removed, squalamine has virtually no effect on the activity of the molecule, even though the molecule is still active as a sodium/proton exchanger.

Applicants have discovered still further uses of squalamine. Specifically, applicants have found that squalamine in combination with conventional cancer treating agents, i.e., cytotoxic chemical and anti-hormonal compounds and radiation treatments, will decrease the size and growth of tumors. Even more significantly, applicants have found that the combination decreases the growth rate of highly proliferative CNS tumors, lung tumors, breast tumors, ovarian tumors, liver tumors, neuroendocrine tumors and prostate tumors and can confer survival advantages.

In the practice of this aspect of the invention, either a cytotoxic chemical compound or an anti-hormonal agent is used in a first tumor treatment procedure, and squalamine is used in a second tumor treatment procedure. The first and second treatments may be administered in any time sequence or even simultaneously. In another embodiment, two or more cytotoxic chemical and/or anti-hormonal agents may be administered simultaneously or sequentially in the first treatment process.

The cytotoxic chemical compound(s) used in the first treatment procedure may be any conventional agent, but it is preferably one of the following agents: a nitrosourea, cyclophosphamide, doxorubicin, epirubicin, 5-fluorouracil, topotecan, irinotecan, carmustine, estramustine, paclitaxel and its derivatives, and cisplatin carboplatin, iproplatin and related platinum compounds. These materials are conventional cancer treating agents which are known to those skilled in this art, as set forth in *Medical Oncology, supra*. One particularly preferred nitrosourea is BCNU, which is also known as "carmustine" or "1,3-Bis(2-chloroethyl)-1-nitrosourea." Cyclophosphamide also is known as N,N-Bis-(2-chloroethyl)-N'-(3-hydroxypropyl)phosphordiamidic acid cyclic ester monohydrate. Doxorubicin also is known as adriamycin.

Well known topoisomerase inhibitors include irinotecan [7-ethyl-10-[4-(1-piperidino)-1-piperidino] carbonyloxycamptothecin], also known as CPT 11, and topotecan [9-dimethylaminomethyl-10-hydroxycamptothecin].

Paclitaxel is available under the tradename "Taxol." Various derivatives of paclitaxel may be used in accordance with the invention, such as taxotere or other related taxanes. Cisplatin, another of the cytotoxic chemical compounds which may be used in accordance with the invention, also is known as cis-Diamminedichloroplatinum. Well known analogues of cisplatin are carboplatin and iproplatin (also known as CHIP[cis-dichloro-trans-dihydroxo-bis[isopropylamine]platinum IV). Those of ordinary skill in the art would be familiar with other specific cytotoxic agents that could be used in the process of the invention.

The anti-hormonal agent used in the first treatment procedure may be any conventional agent, but it is preferably an androgen inhibiting agent. Among the preferred androgen inhibiting agents are LHRH (luteinizing hormone releasing hormone) agonists and anti-androgens such as flutamide, biclutamide, nilutamide, and luprolide. These agents are preferred for the treatment of prostate tumors, but other anti-hormonal agents may be used for other tumors, as would be recognized by those skilled in the art.

In addition, the invention encompasses the use of cytotoxic compounds together with anti-hormonal compounds or the use of two or more of these compounds.

Furthermore, there are no limitations on the chemotherapeutic agent that can be used in this invention. Other conventional chemotherapeutic agents that can be used with squalamine in the process of the invention include methotrexate, melphalan, thiotepa, mitoxantrone, vincristine, vinblastine, etoposide, teniposide, ifosfamide, bleomycin, procarbazine, chlorambucil, fludarabine, mitomycin C, vinorelbine, and gemcitabine.

The first and/or second treatments may be administered by any suitable technique, such as oral, "s.q.,""i.p.,""i.m.,""i.l.," or "i.v." In this application, the terms "s.q.,""i.p.,""i.m.,""i.l.," and "i.v." will be used to refer to subcutaneous administration of squalamine or other substances, intraperitoneal administration of squalamine or other substances, intramuscular administration of squalamine or other substances, intralymphatic administration of squalamine or other substances, and intravenous administration of squalamine or other substances, respectively.

In one embodiment, BCNtJ is delivered to a patient first as a one time intravenous dosage, and thereafter squalamine is injected s.q. twice daily. In another embodiment, cyclophosphamide is the cytotoxic agent. In another embodiment, cisplatin is the cytotoxic agent. In yet another embodiment carboplatin is used in combination with paclitaxel. If appropriate, the cytotoxic chemical compound and the squalamine may be delivered simultaneously by a common pharmaceutical carrier (i.e., one injection including both squalamine and the cytotoxic chemical compound). Other appropriate combinations of administration techniques may be used without departing from the invention. Those skilled in the art will be able to ascertain the appropriate treatment regimens, depending on the cytotoxic chemicals used, the dosages, etc., through routine experimentation.

The squalamine treatment procedure in accordance with the invention also may be used with radiation treatment (i.e., cobalt or X-ray treatment) as the first treatment procedure. In this embodiment of the invention, the first treatment procedure is a radiation treatment, and the second treatment procedure is squalamine administration. Radiation treatments can proceed on a schedule in combination with the squalamine treatments to provide optimum results. Such scheduling of the treatment procedures can be ascertained by the skilled artisan through routine experimentation. Any conventional radiation treatment, such as those described in Medical Oncology, supra., may be used without departing from the invention. In addition to radiation and squalamine treatments, the tumor also may be treated with one or more cytotoxic chemical or anti-hormonal compounds in a third treatment procedure.

The invention will be described below in terms of various specific examples and preferred embodiments. These examples and embodiments should be considered to be illustrative of the invention, and not as limiting the same.

I. PHYSIOLOGICAL PROPERTIES OF SQUALAMINE

A. Antiangiogenic Activity

Squalamine has been demonstrated to be useful as an antiangiogenic agent, i.e., squalamine inhibits angiogenesis. Angiogenesis, the process of forming new blood vessels, occurs in many basic physiological processes, such as embryogenesis, ovulation, and wound healing. Angiogenesis also is essential for the progression of many pathological processes, such as diabetic retinopathy, inflammation, and malignancy (tumor development). In view of its antiangiogenic properties, squalamine may be used for treating various ailments and conditions which depend on angiogenesis, such as those identified above.

Figure 2:
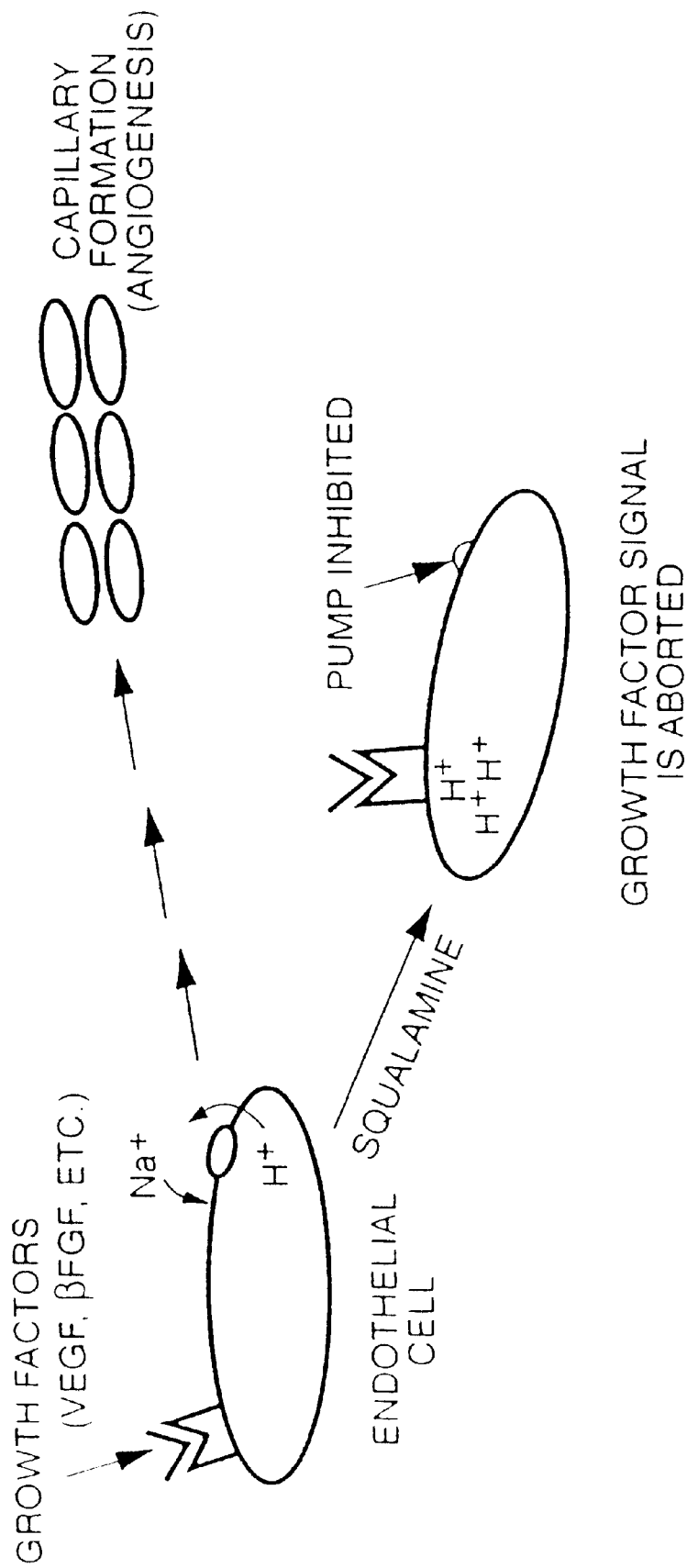
FIG. 2 shows a general overview of the angiogenesis process.

Angiogenesis is a multiple step process which is schematically illustrated in FIG. 2. First, endothelial cells must become activated, for example, by attaching a growth factor such as vascular endothelial growth factor ("VEGF") or basic-fibroblast growth factor ("b-FGF"). The cells then move, divide, and digest their way into adjacent tissue through the extracellular matrix. The cells then come together to form capillaries and lay down new basement membrane. This angiogenesis process is illustrated in the upper portion of FIG. 2. Each of these development stages during angiogenesis is important and may be affected by antiangiogenic agents.

Certain compounds which are believed to be antiangiogenic compounds (i.e., matrix metalloproteinase inhibitors, such as minocycline, SU101 or marimistat) act at later stages in this multistep angiogenesis process. These compounds will be referred to as "downstream" angiogenesis inhibitors. For a discussion of matrix metalloproteinase inhibitors, please refer to Teicher, *Critical Reviews in Oncology/Hematology*, Vol. 20 (1995), pp. 9–39. This document is entirely incorporated herein by reference. In contrast to these known antiangiogenic compounds, squalamine acts at a very early stage in the process by inhibiting the cell activation action of growth factors, i.e., it is an "upstream" angiogenesis inhibitor. As shown in FIG. 2 (toward the bottom), squalamine inhibits the sodium-proton pumps that are normally active and activated by the growth factors. Inhibition of the proton pump places the cell in a quiescent state, and, in this way, capillary formation and angiogenesis is impeded. In effect, the growth factor signal is aborted in the presence of squalamine.

B. Capillary Regression Activity

In addition to antiangiogenic characteristics, squalamine has been shown to have a capillary regression effect in newly formed capillaries. A one time dose (100 ng) of squalamine was applied to capillary beds of young chick embryos that were 2–3 days old. After five minutes, this dose of squalamine appeared to have little effect on the capillary beds. In twenty minutes, however, the capillary bed appeared to be disappearing (i.e., the vessels appeared to be closed off). After forty minutes, additional capillary regression was observed.

The capillary bed also was observed after sixty minutes. At this time, it was noted that some of the capillary vessels were beginning to re-appear, but only the more major vessels were re-appearing. The small vessels were not re-appearing at that time. Four to five days after the one time squalamine treatment, the effect of the squalamine dose was no longer apparent, but newly formed capillaries in the embryos remained susceptible to squalamine induced regression for a limited time while they were newly formed.

From this test, applicants concluded that squalamine-induced capillary regression is reversible, at least with respect to certain capillaries. It also was concluded that squalamine is more effective against small microcapillary blood vessels (i.e., the microvascular bed) as compared to the major blood vessels. Close histological examination of chick microvessels exposed to squalamine revealed vessel occlusion was due to shrinkage of endothelial cell volumes in cells wrapped around the vessel lumen. The applicants postulate that occlusion or regression of small blood vessels by squalamine significantly contributes to the ability of squalamine to impede the flow of nutrients and growth factors into tumors and thereby slows or blocks the rate of growth of the tumors.

C. NHE Inhibitory Activity Of Squalamine

Cell growth and division is necessary for blood vessel and capillary growth and formation. Capillary formation requires a specific extracellular matrix. The NHE antiporter system of a cell is connected to the extracellular matrix. Activation of the NHE antiporter is necessary to induce cell growth, and interference with the NHE antiporter interrupts the matrix signal and interferes with cell growth. When endothelial cell growth is interrupted, capillary growth is impeded.

The NHE antiporter of cells may be activated in different ways. For example, insoluble fibronectin activates the NHE antiporter by clustering and immobilizing Integrin $\alpha_v\beta_1$, independent of the cell shape (the growth of anchorage-dependent cells requires both soluble mitogens and insoluble matrix molecules). In addition, the attachment of stimuli to the extracellular matrix or cell attachment events involving viruses also activate the NHE antiporter.

Figure 3:
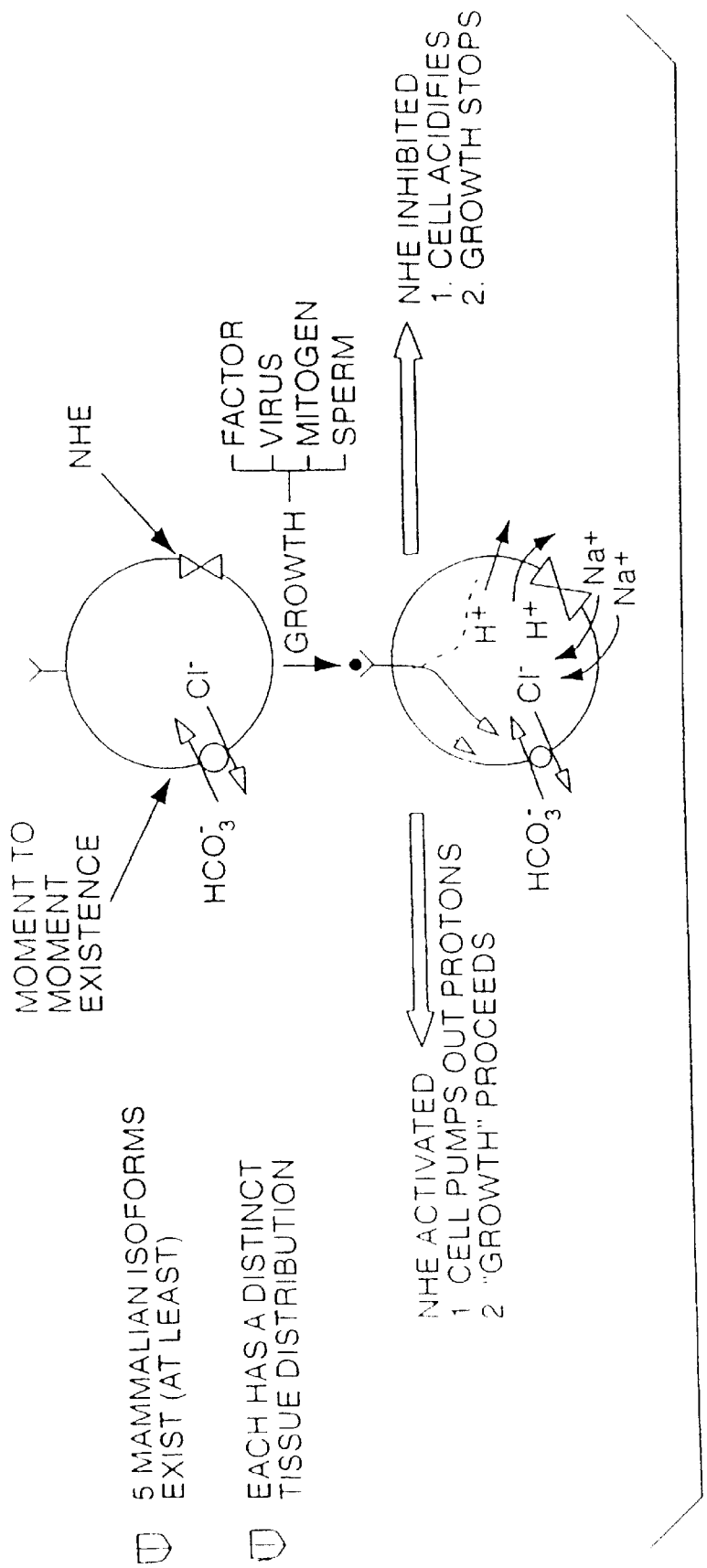
FIG. 3 is a drawing used to illustrate the sodium hydrogen exchanger (NHE) process.

When activated, the NHE antiporter induces cell growth by regulating the pH of the cell. As shown in FIG. 3, the chloride-bicarbonate exchanger and NHE are complementary pH regulators in cells. The chloride-bicarbonate exchanger makes the cell become more alkaline, while NHE contributes to the control of hydrogen ion concentration in the cell. When the NHE is inhibited, the cells become acidic (lower pH) and growth stops. This does not mean that the cell dies; it means only that the cell enters a quiescent state (i.e., it does not divide). If the cell returns to a normal pH, growth may resume. When the NHE is activated, the cell becomes more alkaline (higher pH), it pumps out protons, and growth proceeds. Interaction of various modulatory factors (i.e., serum components, secondary messengers, etc.) with one portion of the cytoplasmic region of NHE activates the antiporter, while interaction with another portion inhibits the antiporter. These portions of NHE are described in Tse, et al., "The Mammalian $Na^+/H^+$ Exchanger Gene Family—Initial Structure/Function Studies," *J Am. Soc. Nephr.*, Vol. 4 (1993), pg. 969, etseq. This article is entirely incorporated herein by reference.

Sodium-proton pumps (NHEs) are responsive to different growth stimuli which activate the pump. As noted above in connection with FIG. 2, the proton pump may be activated by attachment of growth factors (e.g., VEGF and b-FGF) to the cell. Additionally, as shown in FIG. 3, other stimuli, such as virus attachment, addition of various mitogens, sperm attachment to an egg, etc, also can cause NHE activation and alkalinization of the cell. Attachment of these stimuli to the extracellular matrix activates the NHE antiporter of the cell and induces cell growth.

At least five different mammalian isoforms of NHE exist, and each has a distinct tissue distribution. Nonetheless, all act in the same manner. NHE1 is the antiporter found in all tissues. NHE2 and NHE3 are more restrictive in their tissue distribution.

The effect of squalamine on NHE activity was measured to determine which isoforms of NHE were affected by squalamine. NHE activity can be measured under various different cellular conditions. Acid loading a cell activates all of the antiporters and permits measurement of NHE. NHE activity also can be measured after growth factor stimulation of the cell. Additionally, the NHE activity can be measured when the cell is in an unstimulated state, because the antiporters, even if unstimulated, continue to function at a slow, but non-zero rate. In each of these cellular conditions, NHE activity usually is measured in the absence of bicarbonate.

Figure 4:
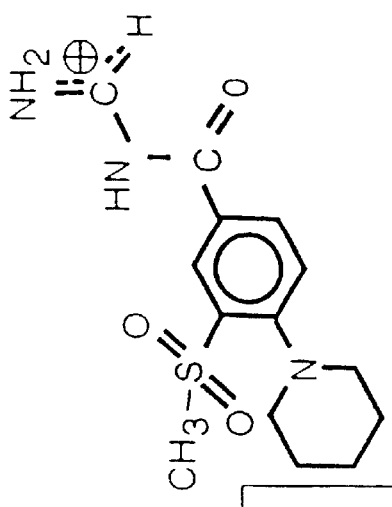
FIG. 4 illustrates the effects of conventional amilorides on inhibiting various isoforms of mammalian NHEs.

Amilorides, which are the classic inhibitors of activated NHE antiporters and which act as direct competitive inhibitors of $Na^+$ ion binding to NHE, do not turn off the antiporter activity in unstimulated cells. As illustrated in FIG. 4, amiloride and amiloride analogues specifically act against NHE1 over NHE2 or NHE3. NHE3 in particular is relatively resistant to inhibition by the amilorides. In contrast to the amilorides, when NHE1 activity was measured in unstimulated melanoma cells, applicants found that squalamine substantially down regulates the activity of the antiporter.

Figure 5A:
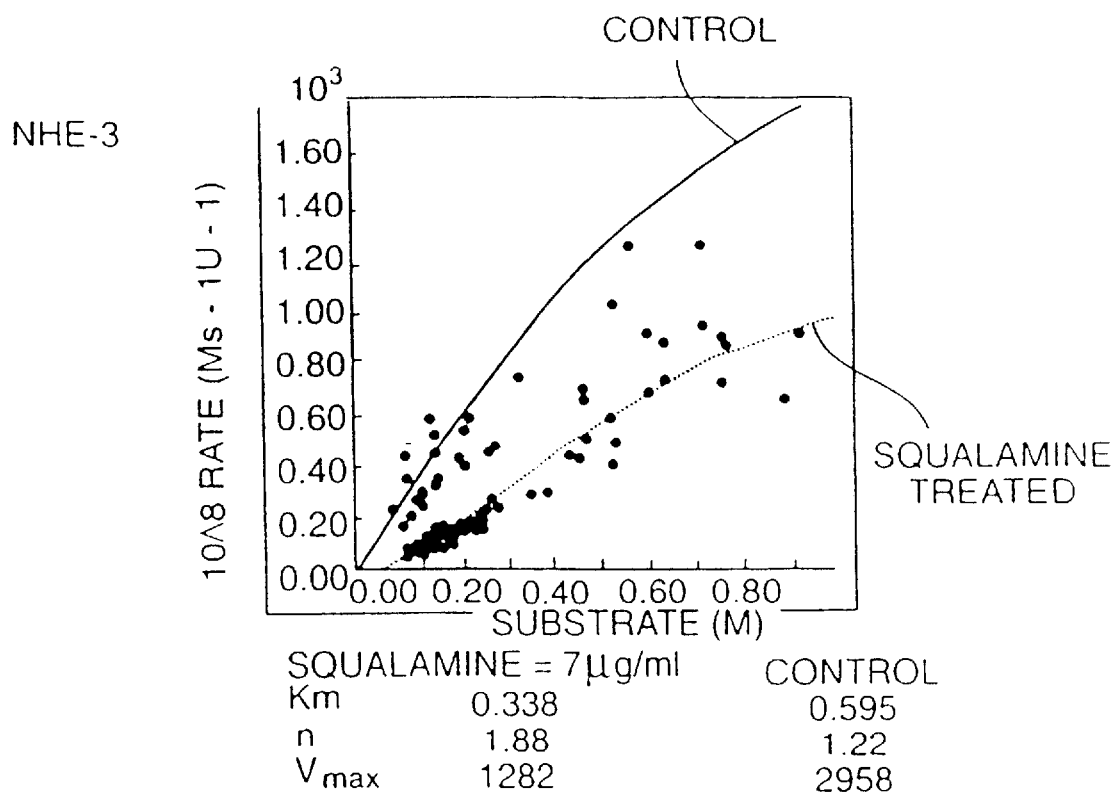
FIGS. 5a and 5b illustrate the effect of squalamine on NHE isoform 3 (NHE3) and NHE1 inhibition, respectively.
Figure 5B:
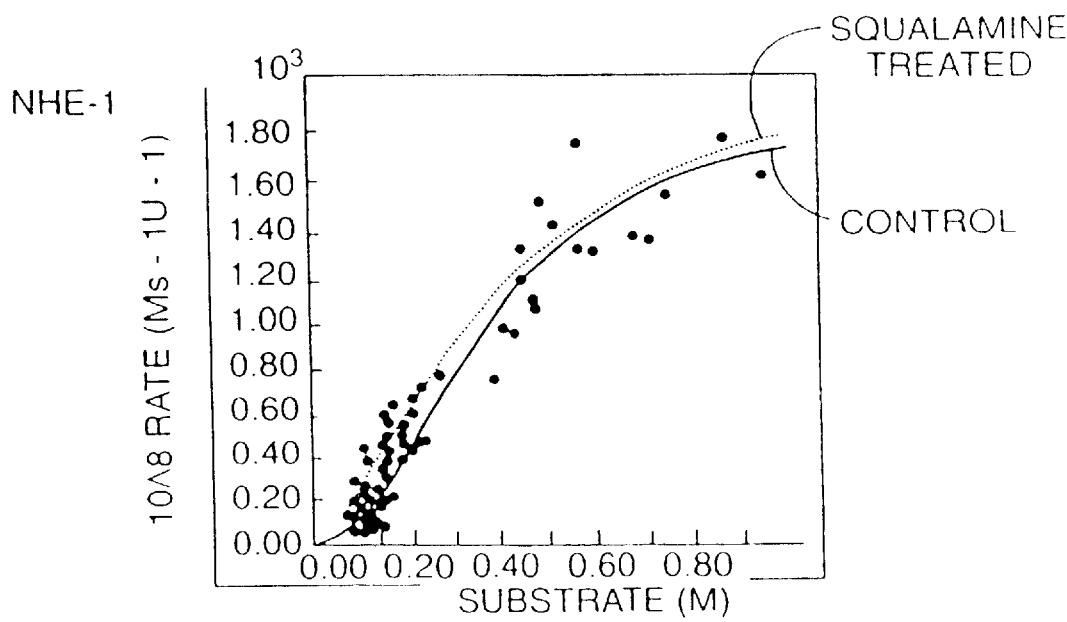
Figure 7:
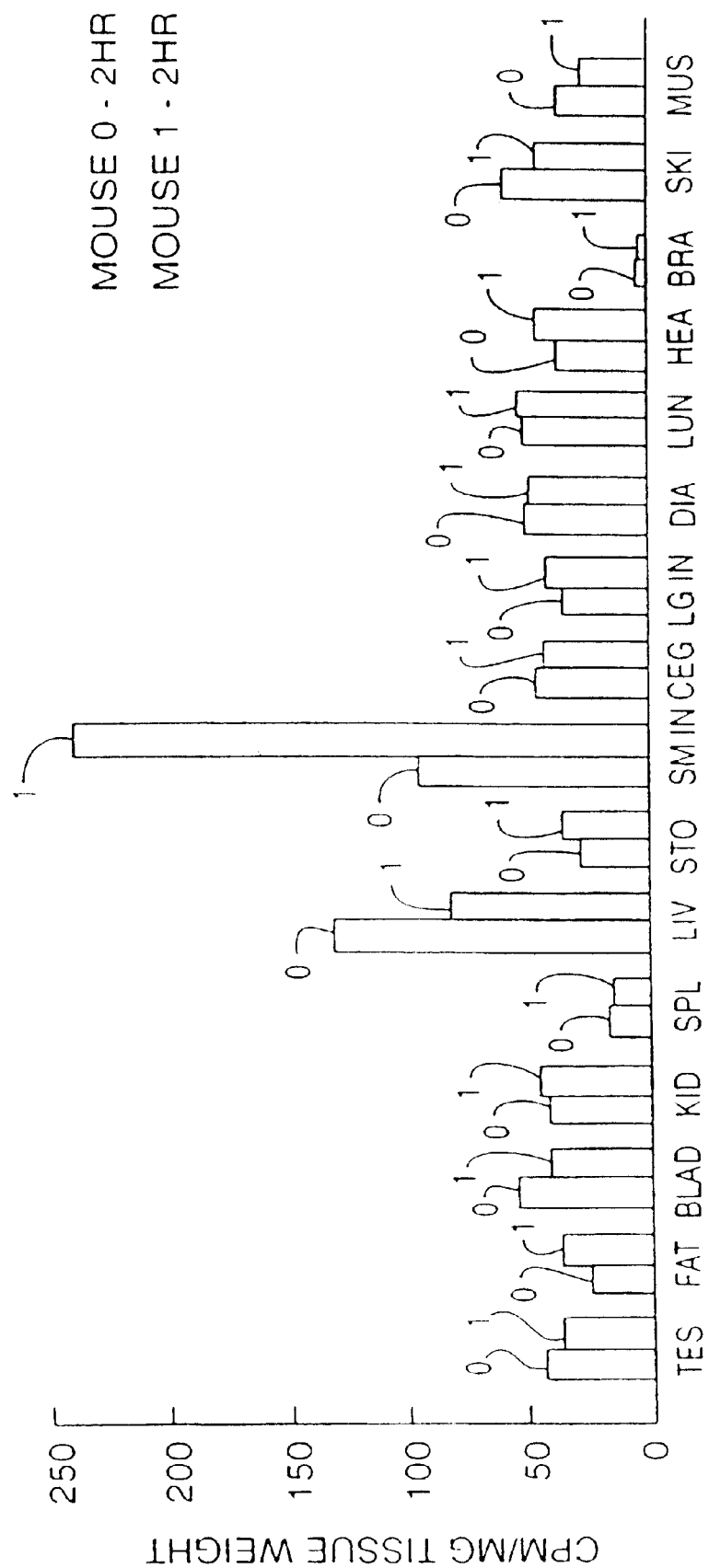
FIG. 7 illustrates squalamine distribution in various tissues after i.v. administration.

The following describes the test used to determine that squalamine inhibits NHE3, but not NHE1 or NHE2. NHE deficient fibroblast cells (PS 120) transfected with an individual human NHE gene were loaded with a pH sensitive dye 2'7'-bis(2-carboxyethyl)-5,6-carboxyfluorescein (BCECF). NHE activity was measured by spectrofluorometric methods using this dye and by amiloride sensitive isotopic $^{22}Na^+$cellular uptake. The cells were acidified by exposure to ammonium chloride in the absence of sodium to eliminate sodium and deactivate the proton pumps. The ammonium chloride was washed out by exposing the cells to tetramethyl ammonium chloride in bicarbonate free medium. The cells were consequently acidified, but in the absence of sodium, the NHE ion pumps did not activate. For this test, as shown in FIGS. 5a and 5b, 7 $\mu$g/ml of squalamine was added to the cells in each case. Sodium then was added back at various concentrations (see the abscissa of FIGS. 5a and 5b) to drive the antiporters (human NHE3 in FIG. 5a and human NHE1 in FIG. 5b). The antiporters were driven at different rates, as evidenced by the cellular pH change rate, depending on the amount of sodium added. As shown in FIG. 5a, when measuring the effect of squalamine on the human NHE3 antiporter, the pH change rate was lower in the squalamine treated cells than the pH change rate in the control group (without squalamine). This indicates that squalamine inhibits human NHE3. In FIG. 5b, however, there is no effective difference in the pH change rate between the squalamine treated samples and the control when measuring the human NHE1 antiporter. From these tests, applicants concluded that squalamine inhibits human NHE3, but not human NHE1. Additionally, in similar tests, it was found that rabbit NHE1 and NHE2 are not affected by squalamine, but rabbit NHE3 is inhibited by squalamine treatment.

In the transfected cells used in this test, it took at least 30 minutes before the NHE3 inhibition effect induced by squalamine was observed. Thus, squalamine did not act like the classic NHE inhibitor amiloride or analogues of amiloride, which are direct competitive inhibitors for sodium and, therefore, act rapidly as NHE inhibitors.

Furthermore, it was observed that the NHE inhibiting effect of squalamine occurred in the absence of lactase dehydrogenase (LDH) leakage from the cell. Because LDH leakage is a non-specific marker of cytotoxicity, it was concluded that squalamine does not have a general cytotoxic effect.

This NHE3 inhibiting activity of squalamine has been mapped to the 76 C-terminal amino acids on the NHE3 molecule. If the 76 C-terminal amino acids of rabbit NHE3 are removed from the molecule, squalamine has been found to have virtually no effect on the activity of the molecule, while the molecule remains active as a sodium/hydrogen exchanger. Thus, the 76 C-terminal amino acids of NHE3 are the site of inhibition by squalamine. It is believed that the squalamine effect on these accessory proteins of NHE3 is tied to an inhibitory effect on tyrosine kinase-dependent activity, although applicants do not wish to be bound by any specific theory of operation.

As noted above, it has been concluded that squalamine inhibits NHE3 and not NHE1. This inhibitory effect of squalamine, however, has been found to work in a manner different from classical and known NHE3 inhibitors. In contrast to squalamine, other inhibitors of NHE3 (e.g., amiloride, amiloride analogues, genestein, calmodulin, and protein kinase C) also inhibit NHE1. Such inhibitors affect only the absolute number of protons that can be secreted by the cell (i.e., "$V_{max}$"), if one looks at the kinetic characteristics of the inhibition. Squalamine, on the other hand, not only inhibits $V_{max}$, but it also forces the cell to fall to a lower pH, as evidenced by a reduction in the Km value. Note the following Table 1, which correlates to data collected in the test of FIG. 5a.

TABLE 1

|  | Squalamine (7 μg/ml) | Control |
| --- | --- | --- |
| Km | 0.338 | 0.595 |
| n | 1.88 | 1.22 |
| $V_{max}$ | 1282 | 2958 |

Thus, squalamine inhibits NHE with nonallosteric kinetics (i.e., nonclassical allosteric inhibition). In additional tests, it also was found that squalamine (at a 1 hour pretreatment) decreased the $V_{max}$ of rabbit NHE3 in a concentration dependent manner (13%, 47%, and 57% with 1, 5, and 7 μg squalamine/ml, respectively). This observed squalamine effect on the $V_{max}$ was time dependent, with a maximum effect occurring at one hour exposure. The observed effect was fully reversible within three hours after removing the cells from the medium.

In view of the test results relating to the effect of squalamine on NHE3, applicants believe that NHE3 is important in maintaining homeostasis of the unstimulated cell. The applicants further believe that prevention of cellular activation by squalamine, especially activation of endothelial cells or precursor cells which participate in formation of new blood vessels during pathophysiological vascularization (such as during tumor growth), is the mechanism through which squalamine inhibits tumor growth.

Applicants have further observed that squalamine changes endothelial cell shape. This suggests that transport proteins which control cell volume and shape may be a squalamine target.

Additional testing of squalamine has indicated that squalamine inhibited brush border membrane vesicle (BBMV) NHE only when the tissue was pretreated with squalamine (51% inhibition at 30 minutes exposure). Direct addition of squalamine to PS 120 fibroblasts during measurement of the exchanger activity had no effect.

D. Pharmacokinetic Studies Of Squalamine

Figure 6B:
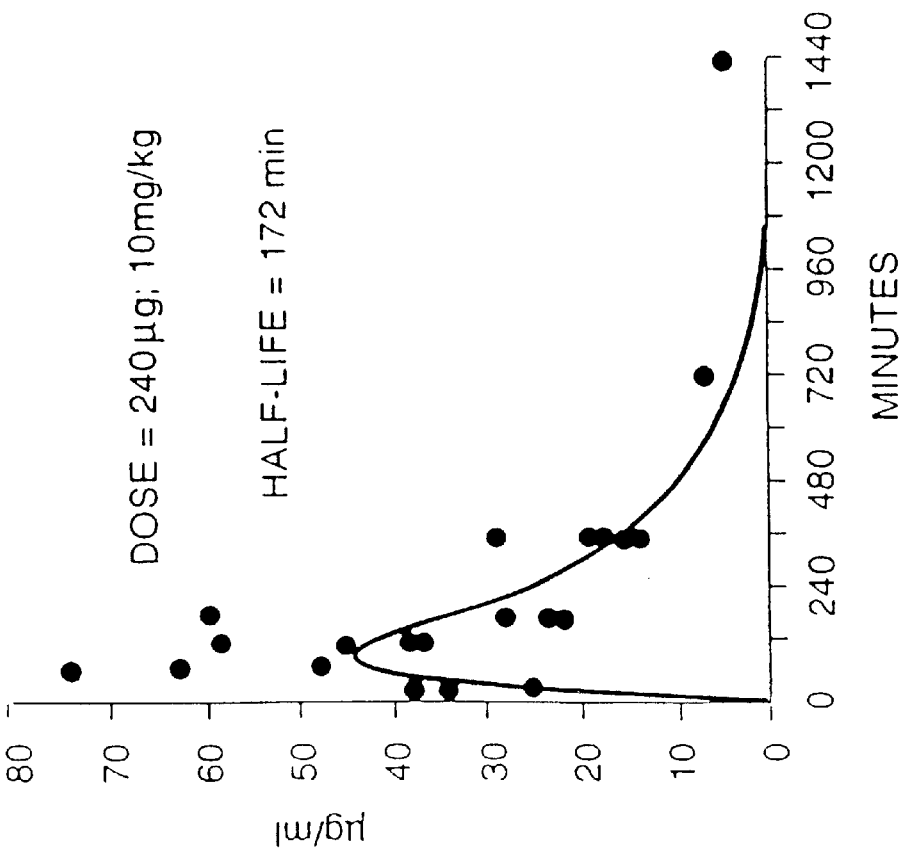
FIGS. 6a, 6b and 6c show the results of a pharmacokinetic study relating to squalamine.
Figure 6A:
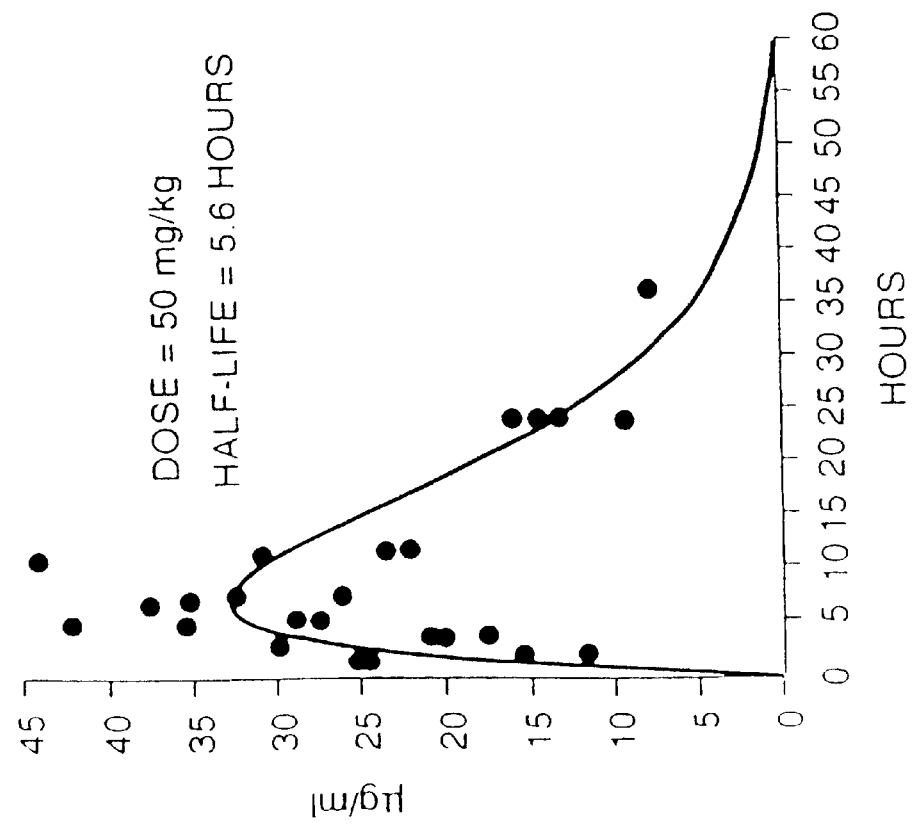
Figure 6C:
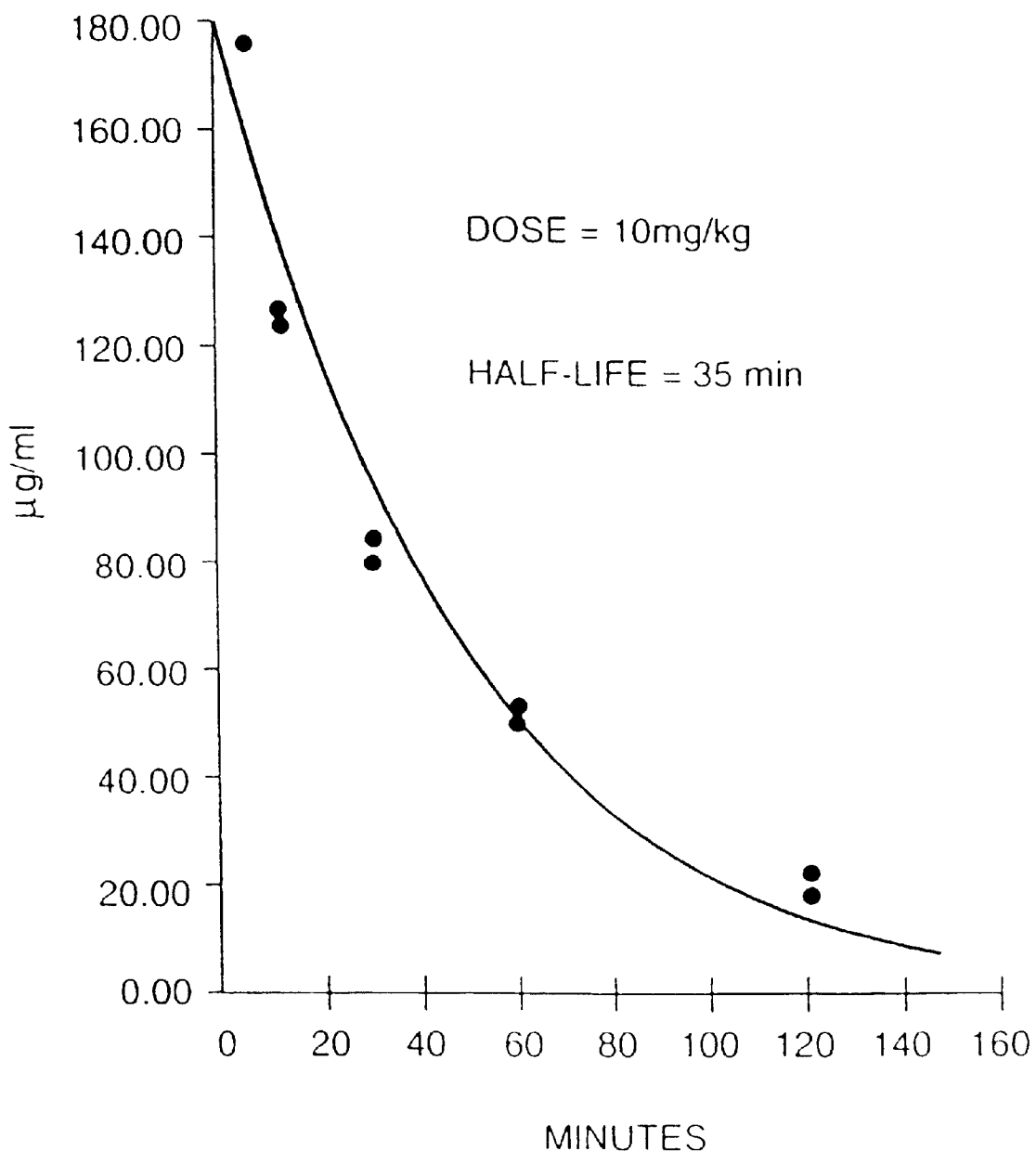

A pharmacokinetic study of squalamine was performed to ascertain the residence time of squalamine in the body. FIGS. 6a to 6c illustrate the test results where squalamine was administered subcutaneously (50 mg/kg, FIG. 6a), intraperitoneally (dose 240 μg; 10 mg/kg, FIG. 6b), and intravenously (10 mg/kg, FIG. 6c). The half-life of squalamine when given intravenously (FIG. 6c) was acceptable (35 minutes), but it was even higher when it was administered intraperitoneally (FIG. 6b, half-life=172 minutes) and subcutaneously (FIG. 6a, half-life=5.6 hours).

In addition to these squalamine half-life tests, applicants have tested to ascertain the distribution of squalamine in a mouse after intravenous administration. FIG. 7 illustrates the distribution of squalamine in mouse tissue two hours after i.v. administration. Some squalamine is contained in most of the tissues, with most of the squalamine concentrating in the liver and the small intestine. The test results shown in FIG. 7 indicate good squalamine distribution. Notably, however, not much squalamine is present in brain tissue. From this, applicants conclude that squalamine probably does not cross the brain/blood barrier. In treating brain tumors, it is believed that the squalamine acts on the endothelial cells in the brain, and in this way, it need not cross the brain/blood barrier The following examples describe more detailed experiments used to test the antiangiogenic characteristics of squalamine in the process of the invention.

II. THERAPEUTIC ADMINISTRATION AND COMPOSITIONS

The mode of administration of squalamine may be selected to suit the particular therapeutic use. Modes of administration generally include, but are not limited to, transdermal, intramuscular, intraperitoneal, intravenous, subcutaneous, intranasal, inhalation, intralymphatic, intralesional, and oral routes. The squalamine compounds may be administered by any convenient route, for example, by infusion or bolus injection, or by absorption through epithelial or mucocutaneous linings (e.g., oral mucosa, rectal, and intestinal mucosa, etc.), and it may be administered together with other biologically active agents. Administration may be local or systemic.

The present invention also provides pharmaceutical compositions which include squalamine as an active ingredient. Such compositions include a therapeutically effective amount of squalamine and a pharmaceutically acceptable carrier or excipient. Examples of such a carrier include, but are not limited to, saline, buffered saline, dextrose, water, oil in water microemulsions such as Intralipid, glycerol, and ethanol, and combinations thereof. The formulation of the pharmaceutical composition should be selected to suit the mode of administration.

The pharmaceutical composition, if desired, also may contain effective amounts of wetting or emulsifying agents, or pH buffering agents. The pharmaceutical composition may be in any suitable form, such as a liquid solution, suspension, emulsion, tablet, pill, capsule, sustained release formulation, or powder. The composition also may be formulated as a suppository, with traditional binders and carriers, such as triglycerides. Oral formulations may include standard carriers, such as pharmaceutical grades of mannitol, lactose, starch, magnesium stearate, sodium saccharine, cellulose, magnesium carbonate, etc.

Various delivery systems are known and may be used to administer a therapeutic compound of the invention, e.g., encapsulation in liposomes, microparticles, enteric coated systems, microcapsules, and the like.

In one embodiment, the pharmaceutical composition is formulated in accordance with routine procedures to provide a composition adapted for intravenous administration to humans. Typically, compositions for intravenous administration are solutions in 5% dextrose and sterile water or Interlipid. Where necessary, the pharmaceutical composition also may include a solubilizing agent and a local anesthetic to ameliorate pain at the site of an injection. Generally, the ingredients of the pharmaceutical composition are supplied either separately or mixed together in unit dosage form, for example, as a dry lyophilized powder or water-free concentrate in a hermetically sealed container such as an ampoule or sachette indicating the quantity of active agent. Where the pharmaceutical composition is to be administered by infusion, it may be dispensed with an infusion bottle containing sterile pharmaceutical grade water, dextrose, saline, or other pharmaceutically acceptable carriers. Where the pharmaceutical composition is administered by injection, an ampoule of sterile water or saline for injection may be provided so that the ingredients may be mixed prior to administration.

The amount of the therapeutic compound (i.e., active ingredient) which will be effective in the treatment of a particular disorder or condition will depend on the nature of the disorder or condition, and can be determined by standard clinical techniques known to those skilled in the art. The precise dose to be employed in the formulation also will depend on the route of administration and the seriousness of the disease or disorder, and should be decided according to the judgement of the practitioner and each patient's circumstances. Effective therapeutical doses may be estimated from extrapolations of dose-response curves derived from in vitro or animal-model test systems.

Suitable dosages for intravenous administration are generally about 1 microgram to 40 milligrams of active compound per kilogram body weight. Suitable dosage ranges for intranasal administration are generally about 0.01 mg/kg body weight to 20 mg/kg body weight. Suitable dosages for oral administration are generally about 500 micrograms to 800 milligrams per kilogram body weight, and preferably about 1–200 mg/kg body weight. Suppositories generally contain, as the active ingredient, 0.5 to 10% by weight of squalamine. Oral formulations preferably contain 10% to 95% active ingredient.

For use of squalamine as an antiangiogenic or cytotoxic agent or in cancer therapies, exemplary dosages are from about 0.01 mg/kg body weight to about 100 mg/kg body weight. Preferred dosages are from 0.1 to 40 mg/kg body weight.

The invention also may include a pharmaceutical pack or kit including one or more containers filled with the pharmaceutical compositions in accordance with the invention. Associated with such containers may be a notice in the form prescribed by a government agency regulating the manufacture, use or sale of pharmaceuticals or biological products, which notice reflects approval by the agency of manufacture, use or sale for human administration.

The conventional cytotoxic chemical and anti-hormonal compounds used in accordance with the invention may be present in any suitable form known to those skilled in the art. These chemical compounds also may be administered by any suitable means also known to those skilled in this art, such as orally, subcutaneously, intravenously, intraperitoneally, intralymphaticly, and intramuscularly.

In describing the invention, applicants have stated certain theories in an effort to disclose how and why the invention works in the manner in which it works. These theories are set forth for informational purposes only. Applicants are not to be bound to any specific chemical or physical mechanisms or theories of operation.

While the invention has been described in terms of various specific preferred embodiments and specific examples, those skilled in the art will recognize that various changes and modifications can be made without departing from the spirit and scope of the invention, as defined in the appended claims. All patents, publications and references referred to throughout this application are herein incorporated by reference in their entirety.

EXAMPLE 1

Rabbit Corneal Micropocket Assay

In determining whether a compound is antiangiogenic, the rabbit corneal micropocket assay is an accepted standard test. In this test, an incision is made in one rabbit cornea, and a stimulus is placed in the incision. The stimulus is used to induce blood vessel formation in the normally avascular corneal region. As one example, a solid tumor in a polymeric matrix can be placed in the cornea as the stimulus because the tumor will release a number of angiogenic growth factors to stimulate new capillary growth. The tumor-derived angiogenic growth factors stimulate the endothelial cells at the scleral junction in the eye to initiate blood vessel growth toward the stimulus. A second polymer pellet (e.g., an ethylene/vinyl acetate copolymer) is placed between the scleral junction and the stimulus. This polymer pellet is either empty (a negative control test pellet), or it contains a compound whose antiangiogenic characteristics are to be tested. The polymer pellet is used to provide a controlled release of the material to be studied. Because of the avascular cornea background in the rabbit cornea, one can visually assess the results qualitatively. In addition, the number of blood vessels can be counted and their length, etc., can be measured to provide a more quantitative evaluation of the results.

The VX2 rabbit carcinoma was implanted in 26 rabbit eyes, in the normally avascular corneal region, to act as an angiogenesis stimulus. Squalamine was incorporated into a controlled release ethylene/vinyl acetate copolymer (20% squalamine and 80% polymer by weight). The loaded polymer pellets were placed in 13 of the corneas to provide a sustained local release of squalamine. Polymer blanks were provided in the remaining 13 eyes as a control. In this manner, one eye of each rabbit served as the squalamine test eye and the other eye of the same rabbit served as the control eye. The eyes were examined weekly using a slit lamp stereomicroscope for three weeks after tumor implantment, and the Angiogenesis Index ("AI") was calculated (this calculation will be described in more detail below with reference to FIG. 8). The squalamine loaded polymer was found in vitro to release active squalamine throughout the treatment period. After the test, the corneas were examined histologically.

Using this test, squalamine was found to be a potent inhibitor of tumor induced capillary formation. Fewer blood vessels were observed in the cornea treated with squalamine as compared to the control cornea, and these vessels were generally shorter than the vessels in the control cornea.

Some of the corneas were then sectioned to observe the effect of squalamine on the tumor cells themselves. The untreated control corneas had many vessels in and adjacent to the tumor. The tumors in the squalamine-treated corneas were still viable (i.e., the tumors were not dead), but there was essentially no vasculature associated with those tumors. Thus, the squalamine-treated tumors had greatly diminished vascularity as compared to the corresponding control tumor sections. These findings suggested that squalamine works against the blood vessels, and not against the tumor itself.

Figure 8:
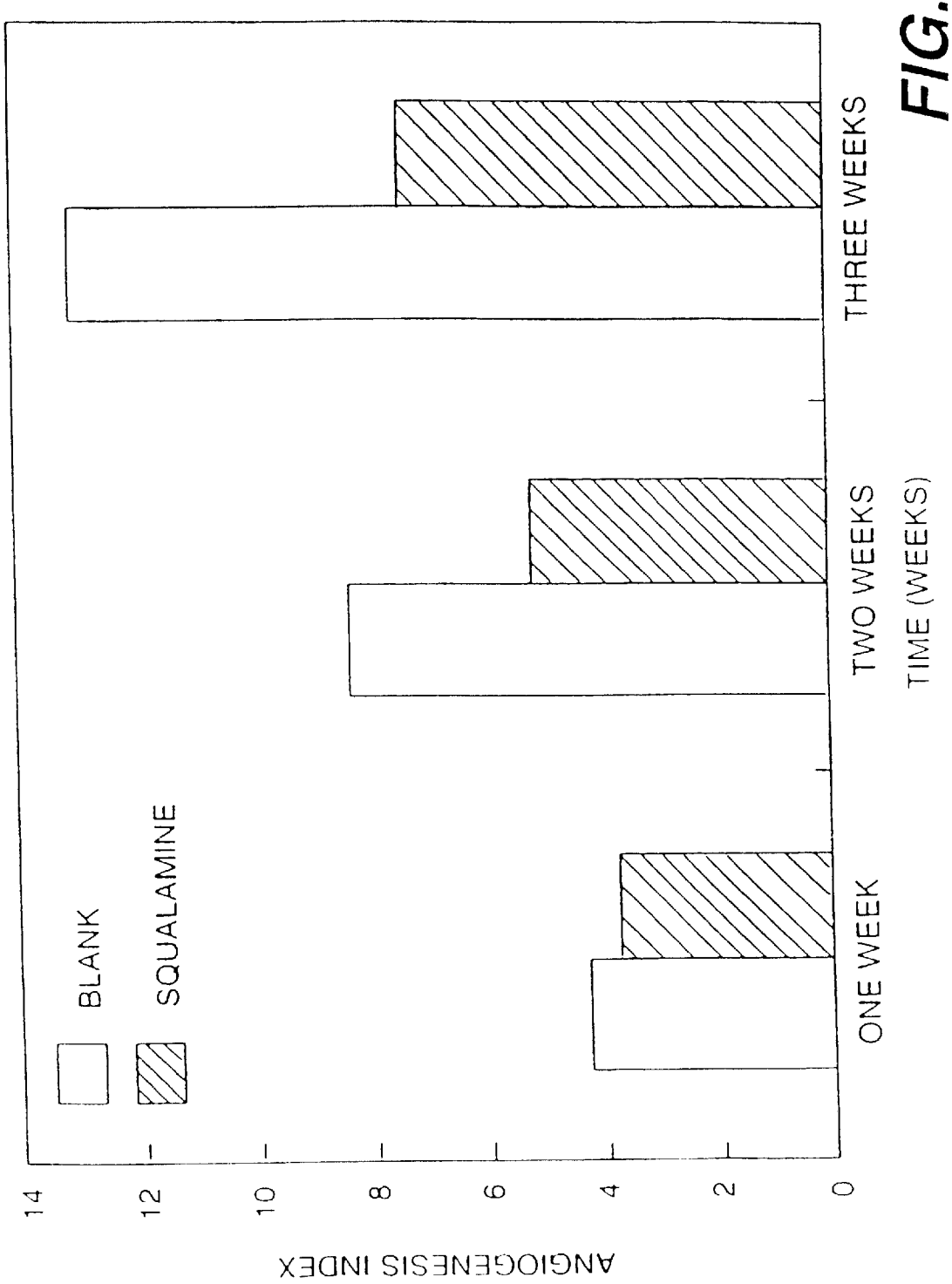
FIG. 8 shows an angiogenesis index using squalamine as determined in the rabbit corneal micropocket assay.

FIG. 8 shows a graphical representation of the results of the rabbit cornea micropocket assay test. To provide a quantitative evaluation, the Angiogenesis Index ("AI") of each eye was determined. To determine the Angiogenesis Index, first the vessel density ("$D_{vessel}$") in an eye was graded on a 0–3 scale as follows:

TABLE 2

$D_{vessel}$ Value Determinations

| $D_{vessel}$ Value | Visual Observation |
|---|---|
| 0 | No vessels present |
| 1 | 1–10 vessels present |
| 2 | >10 vessels present, but loosely packed |
| 3 | >10 vessels present, packed densely |

The vessel length ("$L_{vessel}$") was then measured in each cornea. The vessel length is the length of the longest vessel measured from the cornea-scleral junction to the distal edge of the longest vessel growth. The Angiogenesis Index then is determined from these measurements by the following equation:

$$AI = D_{vessel} \times L_{vessel}.$$

FIG. 8 shows the mean Angiogenesis Index for each group of corneas (squalamine treated and untreated) in the rabbit cornea micropocket assay after 1, 2, and 3 weeks. As shown in the figure, squalamine was very inhibitory to the growth of new blood vessels. The squalamine treated eyes showed a significantly reduced AI value as compared to the untreated eyes (37% reduced at Day 14 ($p=0.05$, Wilcoxon rank sum test) and 43% reduced at Day 21 ($p<0.01$)). This data illustrates that squalamine inhibits tumor induced growth of new blood vessels or capillaries over a long time period. More specifically, squalamine exhibits high antiangiogenic activity even after three weeks.

EXAMPLE 2

Squalamine Does Not Cause Inflammation

In the rabbit corneal micropocket assay test, if the rabbit cornea becomes inflamed, this inflammation can lead to the formation of new blood vessels in the cornea. Such inflammation would skew the test results. Therefore, tests were conducted to determine whether squalamine, in and of itself, was responsible for any inflammatory response in the cornea. Several non-bioresorbable ethylene/vinyl acetate copolymer pellets were loaded with different concentrations of squalamine, namely, 2%, 10%, and 20% squalamine, by weight. These pellets were then placed in rabbit corneas which did not include an angiogenic stimulus. Squalamine did not induce inflammation at any of these concentrations. Thus, squalamine does not lead to the generation of new blood vessels by inflaming the cornea.

EXAMPLE 3

Squalamine Use In Brain Tumor Treatment

The rabbit corneal micropocket assay test results suggested to applicants that squalamine may be a potent antiangiogenic agent that inhibits neovascularization. Recognizing that the exponential growth of solid tumors in the brain is dependent on neovascularization, applicants assessed the activity of squalamine in an animal model on the growth of solid tumors in the brain.

Of solid brain tumors, malignant gliomas are the most common form of cancerous tumors. These tumors are the third leading cause of death from cancer in young adults between the ages of 15 and 34. Malignant gliomas are characterized by their ability to induce the normally quiescent brain and/or CNS endothelial cells into a highly proliferative and invasive state. The gliomas express vascular endothelial growth factor ("VEGF") and other growth factors which stimulate inducible receptors on CNS endothelial cells in a paracrine manner (i.e., the VEGF originates from the tumor cell and stimulates the endothelial cells). The CNS endothelial cells subsequently initiate angiogenic invasion and thus provide nourishment of the glioma. Applicants tested the antiangiogenic activity of squalamine against gliomas by testing (1) its ability to selectively inhibit VEGF-mediated stimulation of endothelial cells and (2) its effect against experimental murine glial tumors.

In vitro tests were first performed to determine that squalamine acts specifically on endothelial cells. Applicants used endothelial cells because such cells are involved in the early steps of angiogenesis, as described above in conjunction with FIG. 2. Specifically, tumor angiogenesis is a series of sequential and overlapping steps. First, the endothelial cells activate and proliferate. Then, proteolytic enzymes are produced and the cells migrate. New basement membranes must then be generated. In this manner, new blood vessels are generated and tumor size increases.

In conducting this in vitro analysis, the following cell lines were tested: (a) bovine retinal endothelial cells; (b) 9L and C6 rat glioma cells; (c) human H80 glioma cells; and (d) VX2 rabbit carcinoma cells (the same type as the tumors implanted in the rabbit corneal micropocket assay test described above). The endothelial mitogen which was used in this analysis was VEGF at a concentration of 20 ng/ml.

The cells were allowed to attach overnight to tissue culture plates containing an optimized growth media. Following attachment, the cells were exposed to solvent only or to increasing concentrations of squalamine (0, 10, 20, 30, 60, and 90 μg squalamine/ml). Cell growth was counted daily for three days using a Coulter Counter. A total of 10,000 cells per well were plated and each experimental concentration was tested in quadruplicate. The results were then averaged. The bovine retinal endothelial cells were grown and treated in an identical manner to the other cell lines, except that the growth of these cells was measured after the addition of 20 ng/ml of human recombinant VEGF to the cells prior to the squalamine treatment.

Cell proliferation by all tumor lines and by endothelial cells not treated with VEGF was statistically unaffected after exposure for 24 and 48 hours to squalamine concentrations up to 30 μg/ml. Growth of the VEGF-stimulated endothelial cells, however, was significantly reduced by squalamine at these same times in a concentration dependent manner.

Percentage endothelial cell growth inhibition (%I) was determined by the following equation:

$$\frac{(\text{\# of cells in control sample} - \text{\# of cells in experimental sample}) \times 100}{(\text{\# of cells in control sample})} = \% I$$

The following Table shows the results at 48 hours for the VEGF-stimulated endothelial cell line.

TABLE 3

Percent Inhibition Data

| Squalamine Conc. | % Inhibition (average) |
|---|---|
| 10 µg/ml | 38% (p < 0.01) |
| 20 µg/ml | 57% (p < 0.001) |
| 30 µg/ml | 83% (p < 0.001) |

Figure 9:
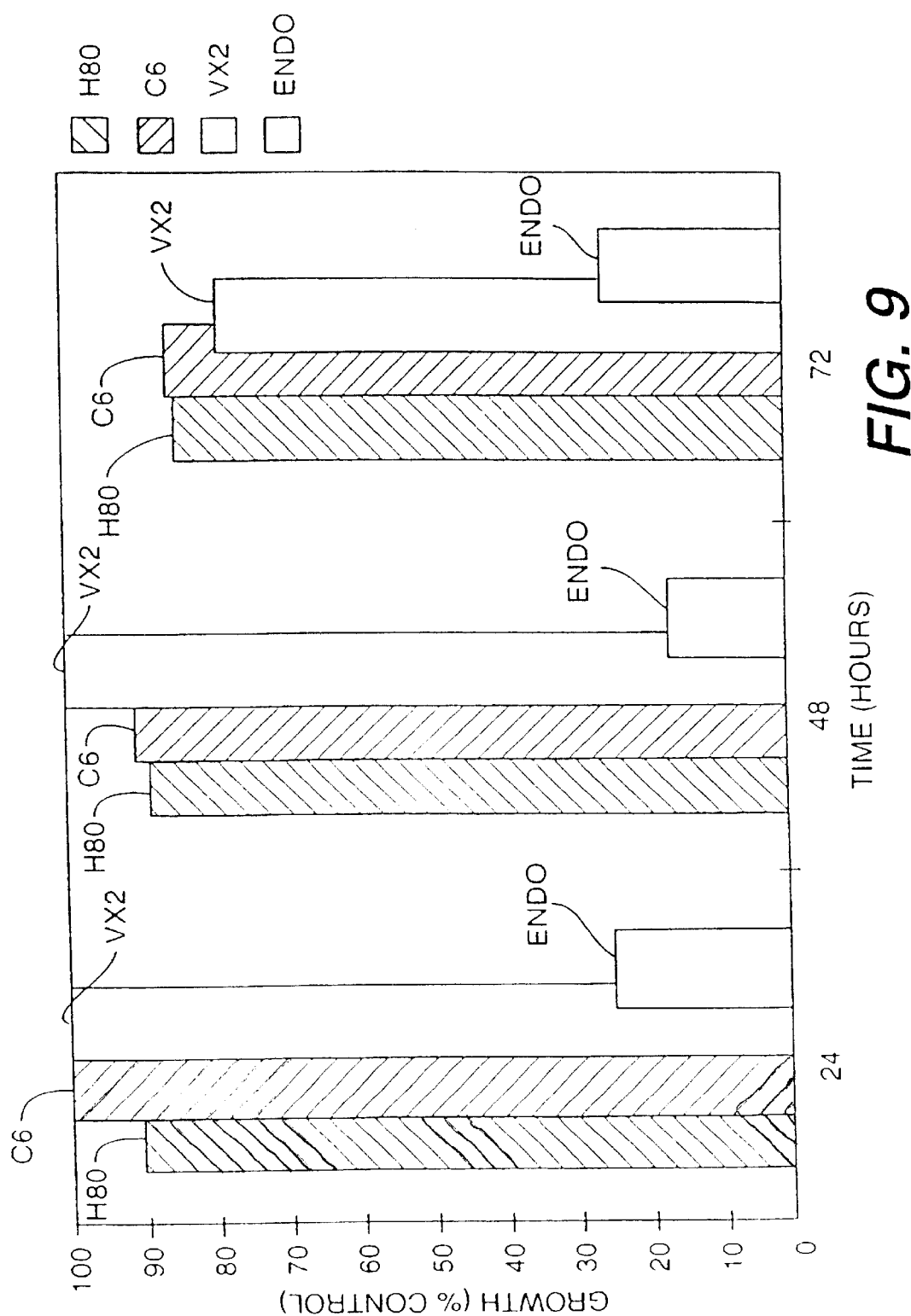
FIG. 9 shows the inhibitory effect of squalamine on growth of endothelial cells as compared to tumor cell lines.

Additional data is illustrated in FIG. 9. This figure shows the growth of the various cell lines as a percentage of the growth in the control groups for in vitro administration of squalamine at 30 µg/ml after 1, 2, and 3 days. As shown in FIG. 9, growth is reduced for the VEGF-stimulated endothelial cells specifically, while the growth in the other cell lines (H80, C6, and VX2) is not dramatically affected.

Based on this information, applicants concluded that squalamine dramatically and specifically inhibits VEGF-stimulated growth of endothelial cells in vitro. Thus, squalamine is a potent inhibitor of tumor-induced angiogenesis, and this effect appears to be precipitated through specific inhibition of endothelial cell proliferation induced by VEGF. Thus, squalamine is believed to be well suited for reducing or diminishing the neovasculature induced by tumors for use in tumor specific antiangiogenic therapy.

In addition to inhibiting VEGF-stimulated growth of endothelial cells, squalamine also has been found to interfere with growth stimulation in human brain capillary endothelial cells induced by b-FGF, $PDGF_{bb}$, scatter factor (HGF or hepatocyte growth factor), conditioned tumor media, and human brain cyst fluid. Thus, as the tumor puts out a variety of different growth factors, squalamine has an inhibitory effect on several.

Figure 10:
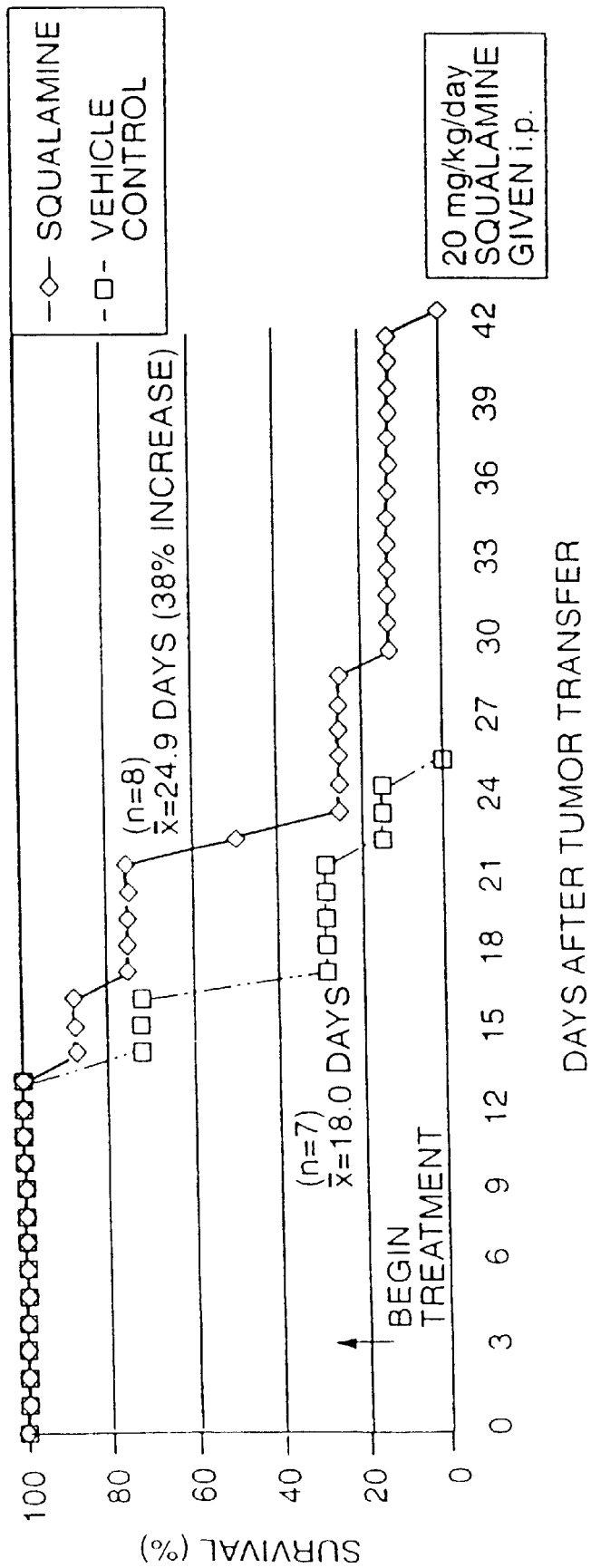
FIG. 10 illustrates survival test results using squalamine in a glioma lethality study with a rat 9L glioma introduced into the brains of healthy rats.

In view of these test results, applicants tested squalamine in an animal model for brain cancer. To test the effect of squalamine on tumors located in the brain, small sections (1 $mm_3$) of existing rat gliomas were taken from rat flanks where they were being maintained and were implanted into the rat brains in two groups of rats. Thus, in this model, the tumors were viable when placed in the rat brain. Three days after implantation, and after some vasculature had developed, treatment with 20 mg/kg/day of squalamine (i.p.) was initiated in one group of rats. The control animals ("vehicle control" in FIG. 10) were given the carrier vehicle only (no squalamine), and the other animals were treated with squalamine ("Squalamine" in FIG. 10). As shown in the figure, the animals treated with squalamine had a 38% increase in mean survival time ($\bar{x}$=24.9 days v. $\bar{x}$=18.0 days). FIG. 10 further illustrates that in this animal model, the squalamine treated rats, in general, had an increased survival time.

A squalamine toxicity test was performed in another animal model. Conventional cytotoxic chemical compounds are quite toxic. For example, BCNU, which is a conventional chemotherapy agent, has a cumulative toxicity effect. For this reason, it is administered only one time to a patient. The use of BCNU is described on pages 304 and 305 of Calabresi in *Medical Oncology, supra*. In order to test the toxicity of squalamine, a group of rats was given a daily squalamine dose of 20 mg/kg/day (i.p.) for more than 30 days and maintained for up to 200 days following dosing. The animals in this study remained healthy. This result indicates that squalamine has little or no toxicity.

EXAMPLE 4

Squalamine Use With Conventional Cancer Treatments

As described above, squalamine is an upstream inhibitor of the angiogenesis process by inhibiting the activation of endothelial cells after growth factor interaction. Because of its angiogenesis inhibiting properties, squalamine has been demonstrated to be effective in treating solid tumors which rely on neovascularization to proliferate. Applicants tested to determine whether beneficial results could be obtained when treating tumors by combining a squalamine treatment (an upstream angiogenesis inhibitor) with a conventional cancer treatment using an alkylating agent.

a. The Squalamine 9L Glioma Flank Study

Four groups of rats (twenty total Fisher 344 rats, 200 g) were given s.q. transplants of 1 $mm_3$ 9L gliosarcoma tumors (9L glioma) on Day 0. The tumors were implanted in the rat flanks to avoid complications relating to adequate brain levels of squalamine. Randomization and treatment began on Day 5 according to the following scheme:

TABLE 4

Treatment Conditions

| Group No. | Treatment |
|---|---|
| 1 | Saline (control group) |
| 2 | One time dose of 14 mg/kg BCNU given i.p. on Day 5 |
| 3 | Squalamine - 20 mg/kg given s.q. B.I.D.[1] |
| 4 | One time dose of 14 mg/kg BCNU given i.p. on Day 5 and daily injection of squalamine - 20 mg/kg given s.q. B.I.D- beginning on Day 5. |

[1]The term "B.I.D." means that the component is administered twice a day (10 mg/kg given at two different times each day).

On Day 25 or 26 after tumor implantation, the tumor size was measured directly. The tumor size (i.e., its volume "V") was estimated based on volumetric calculations determined from the measured length ("L"), width ("W"), and height ("H") of the tumor ($V_{tumor\ spheroid}$~0.5 ×L×W×H). Table 5 summarizes the results. The tumor volumes shown in Table 5 represent the mean tumor volumes for each treatment group for those animals that survived to the end of the experiment.

TABLE 5

Tumor Volumes

| Group No. | No. of Animals | Mean Tumor volume ($mm^3$) | % Reduction (based on control volume) |
|---|---|---|---|
| 1 | 5 | 18,324 | — |
| 2 | 6 | 2,547 | 86.1% |
| 3 | 5 | 3,347 | 81.7% |
| 4 | 4 | 38 | 99.8% |

Table 5 illustrates the advantageous results achieved when treating tumors with the combination of squalamine and the nitrosourea BCNJ (Group 4). A 99.8% reduced mean tumor size was observed when treating with both squalamine and BCNU in this group. Table 5 further shows that squalamine alone (Group 3) was effective in treating the tumor. The tumor size was reduced by 81.7% in Group 3, as compared to the control group.

Applicants conclude that the use of squalamine in combination with conventional cytotoxic chemical compounds can slow or halt the spread of brain cancers. The tumor itself shrinks and becomes necrotic. It is expected that combined squalamine and cytotoxic chemical treatment will extend survival. Thus, this treatment potentially will allow management of brain cancers.

b. Squalamine Use in Breast Tumor Treatment

Figure 11:
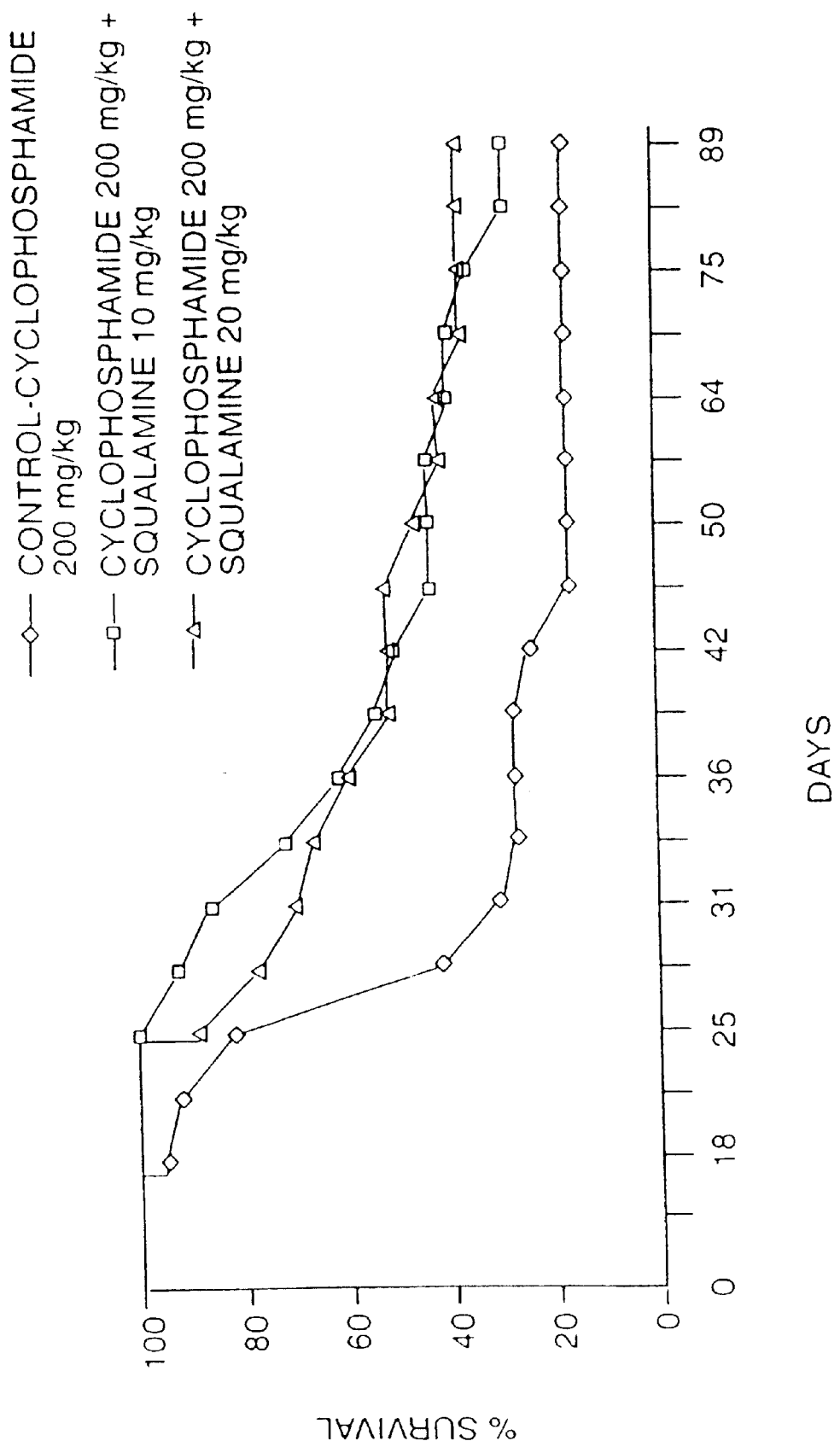
FIG. 11 shows the survival of mice carrying human MX-1 breast tumor xenografts and treated with squalamine subsequent to cyclophosphamide treatment.

The human MX-1 breast cancer line has previously been used to document in vivo activity of cyclophosphamide and other cytotoxic chemotherapeutic compounds either as single agents or in combination (T. Kubota, et al., *Gann* 74, 437–444 (1983); E. Kobayashi, et al., *Cancer Research* 54, 2404–2410 (1994); M.-C. Bissery, et al., *Seminars in Oncology* 22 (No. 6, Suppl. 13), 3–16 (1995)). These documents each are entirely incorporated herein by reference. Squalamine was examined as adjunctive therapy following a single 200 mg/kg dose of cyclophosphamide. The cyclophosphamide was injected on day 14 following implantation of the tumor, at a time when the tumors measured 65–125 μl. The cyclophosphamide caused partial regression in all animals and complete regression in a small fraction of the animals. The animals were then randomized to three treatment arms (each n=27): vehicle dosing only (Intralipid); squalamine given 10 mg/kg/day in Intralipid; and squalamine given 20 mg/kg/day in Intralipid for five days a week. Animals whose tumors exceeded 2 grams at any time during the experiment were euthanized. The experiment was continued for 90 days after initiating squalamine treatment to ensure that only mice experiencing long-term cures were still alive. The high dose squalamine was discontinued after five weeks of treatment because of animal weight loss and potential toxicity concerns, so these animals did not receive squalamine for the last eight weeks of the experiment. The low dose squalamine treatment produced a significant (P<0.01) inhibition in the rate of progression of the breast tumors at all times examined (FIG. 11). The high dose squalamine treatment produced significant (P<0.05) delay in progression of the breast tumors only at 30 days post-initiation (i.e., only while squalamine was still being given), but high dose squalamine also doubled the long-term cure rate in these animals compared to controls which received cyclophosphamide alone (FIG. 11). Examination of the history of the long-term cure animals which received cyclophosphamide and high dose squalamine revealed that the additive effects of squalamine were manifested within two weeks after starting squalamine treatment.

c. Squalamine Use in Lung Tumor Treatment

Figure 12:
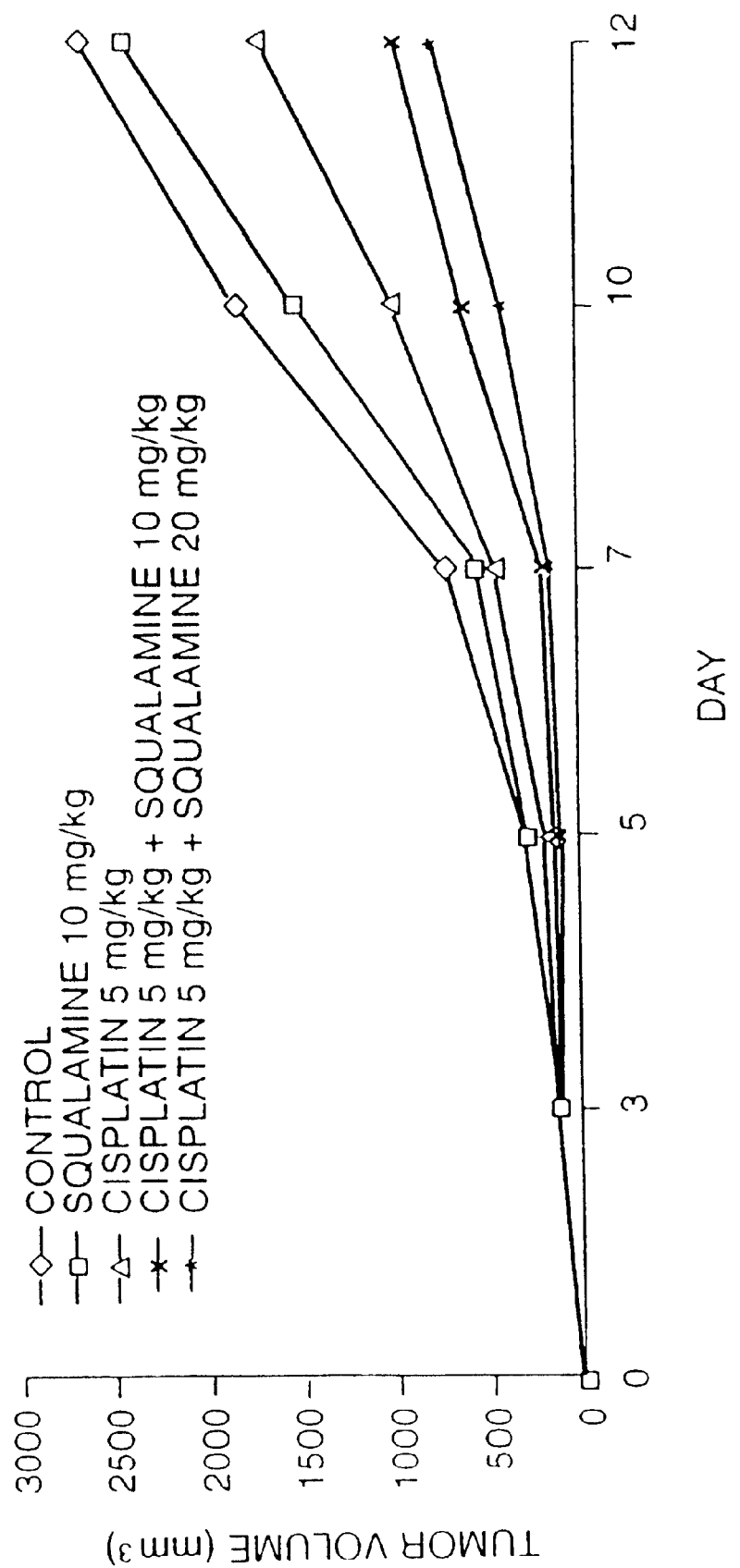
FIG. 12 depicts the inhibition of a human lung adenocarcinoma (H460) in a mouse xenograft-combination therapy study with squalamine and cisplatin.

Studies in a nude mouse xenograft model of lung cancer have been carried out using several human lung cancer lines which differ in their growth rate. The data collected show that squalamine has synergistic activity in combination with cisplatin (e.g., FIG. 12). The experimental lung cancer model design involves subcutaneous injection of $5 \times 10^6$ tumor cells followed by a single injection of the chemotherapeutic drug on day 3 or 4. Daily intraperitoneal squalamine injections with 20% Intralipid as a vehicle began the following day for some groups of mice and continued until the experiment was terminated 7–14 days later. Groups of mice receiving squalamine alone started receiving the aminosterol on the same day as aminosterol treatment in the combination chemotherapy groups. Tumor volumes were then determined at termination of the experiment and compared. It was found for both the aggressively growing H460 human lung adenocarcinoma line and for the more slowly growing Calu-6 human lung adenocarcinoma line that squalamine had minimal effects on tumor growth as a monotherapeutic agent when started on day 4 or 5, but could contribute to growth inhibition if it were started on day 1. However, when used starting on day 4 or 5, in combination with cisplatin, given at or near a maximum tolerated dose, squalamine significantly and reproducibly improved tumor growth inhibition over cisplatin alone in a dose-dependent fashion for both the H460 and Calu-6 cell lines.

d. Squalamine Use in Metastatic Lung Cancer

The murine Lewis lung adenocarcinoma was implanted subcutaneously in the hind-leg of male C57BL/6 mice and allowed to grow for one week. Groups of mice were then left untreated or treated with either squalamine (20 mg/kg/day, s.c.), cyclophosphamide (125 mg/kg, i.p. on days 7, 9 and 11), cisplatin (10 mg/kg, i.p. on day 7), the combination of squalamine and cyclophosphamide, or the combination of squalamine and cisplatin. On day 20, the animals were sacrificed, and the mean number of lung metastases were determined for each group. All treatments reduced the number of metastases; however, the most effective treatments were the combination of squalamine with either of the cytotoxic agents (FIG. 13).

EXAMPLE 5

In Vitro Studies of Squalamine on Human Prostate Tumor Cell Growth

Prior to in vivo studies, applicants evaluated the therapeutic potency of squalamine on human prostate cancer cells in vitro.

The anti-proliferative effect of squalamine was evaluated in tissue culture by both crystal violet staining and [$^3$H]-thymidine incorporation, on the LNCaP/C4-2 human prostate cancer progression model. Developed by applicants' laboratory, this lineage-derived cell line recapitulates the progression of human neoplastic prostate disease from an androgen-dependent and minimally metastatic condition (LNCaP cells) to an androgen-independent (defined as being able to proliferate in castrate hosts) and highly aggressive state (C4-2 subline). The LNCaP/C4-2 progression model has been previously demonstrated to be an effective model for screening the efficacy of therapeutic agents for prostate cancer.

Figure 14A:
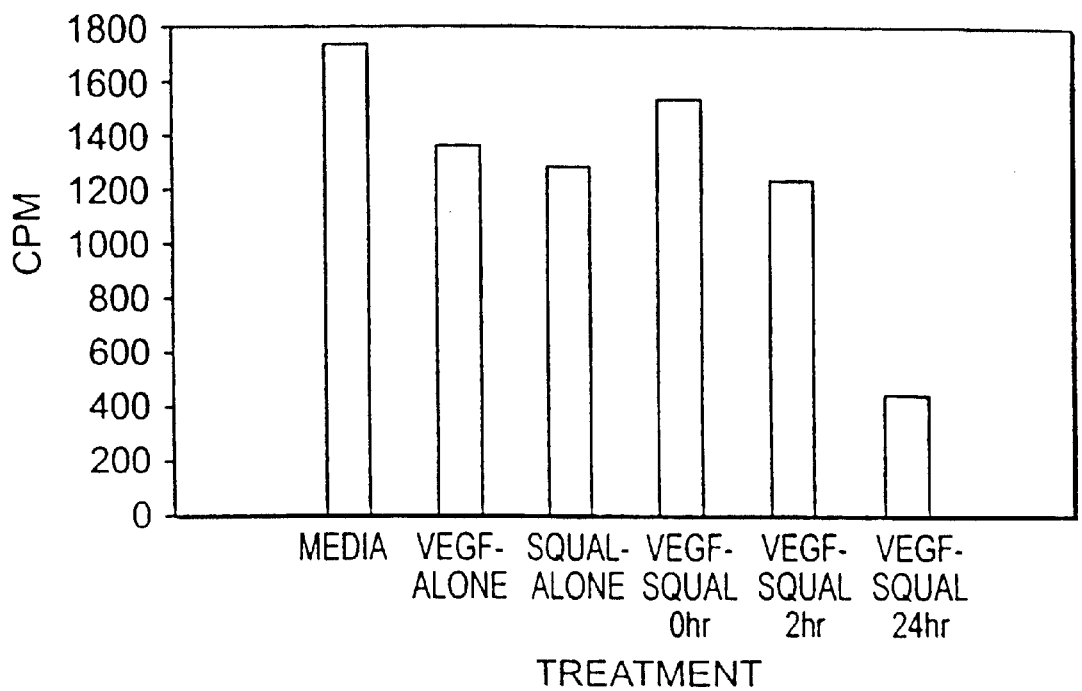
FIGS. 14a and 14b illustrate the effect of squalamine, VEGF, and a combination of VEGF and squalamine treatment on LNCaP human prostate cell growth.
Figure 14B:
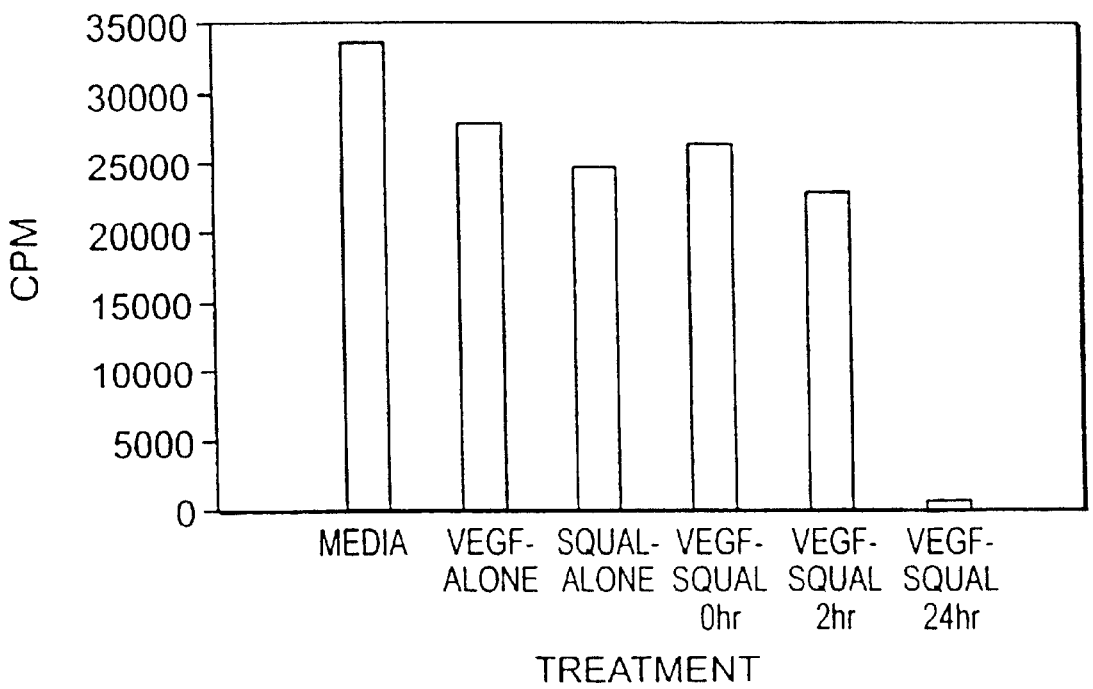

By itself squalamine had a nominal effect on the growth of either the parental LNCaP or lineage-derived C4-2 cells. However, as demonstrated in FIG. 14, with the addition of exogenous VEGF (supplied by Genitech Corporation, South San Francisco, Calif.), both LNCaP (FIG. 14a) and, to a greater extent, C4-2 proliferation (FIG. 14b) was inhibited. Visually, the outcome appeared to result from tumor cell destruction, rather than from decreased growth. Later studies (data not shown) suggest that this effect is both time-and dose-dependent, with increasing amounts of and exposure to VEGF yielding enhanced results. Furthermore, this synergistic effect appears to be predicated on an initial exposure to VEGF, followed by subsequent exposure to squalamine, and not the reverse (data not shown).

EXAMPLE 6

In Vivo Studies on the Therapeutic Effect of Squalamine on Prostate Tumor Growth and Dissemination in a Human Prostate Cancer-Mouse Xenograft Model LNCaP cells admixed with Matrigelm were implanted subcutaneously in 52 athymic mice. Those that developed measurable tumors and sufficient elevations in serum prostate specific antigen ("PSA") (measured using a standard commercially available kit such as from Abbott Diagnostics (St. Louis, Mo.)) underwent orchiectomy. Subsequent to castration, these animals were distributed among the four groups (1–4) outlined below: and an additional control cohort of mice which were castrated but never treated with squalamine.

Figure 15A:
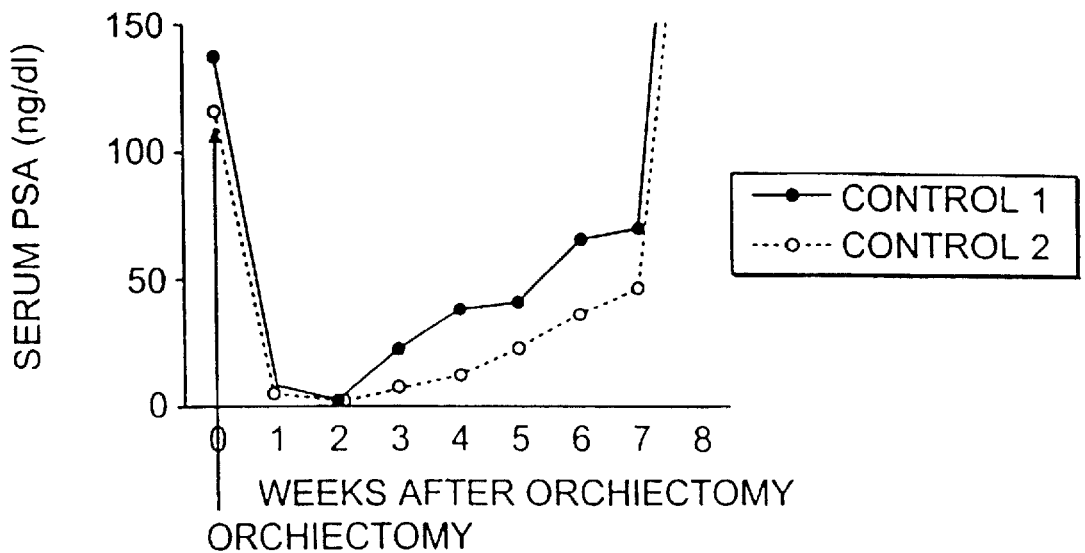
FIGS. 15a and 15b illustrate the effect of squalamine on PSA levels (a) and tumor growth (b) in control athymic mice post-orchiectomy.

In the majority of animals, PSA levels fell to zero at time of castration. By three weeks they began to rebound and continued to rise steadily until the animals succumbed or were sacrificed. In these same mice, tumor size tended to plateau at time of orchiectomy, before beginning to increase in size correspondingly with PSA rebound. The serum PSA curve and tumor volume measurements from two members of this last control cohort are illustrated in FIG. 15a and b, respectively.

Figure 15B:
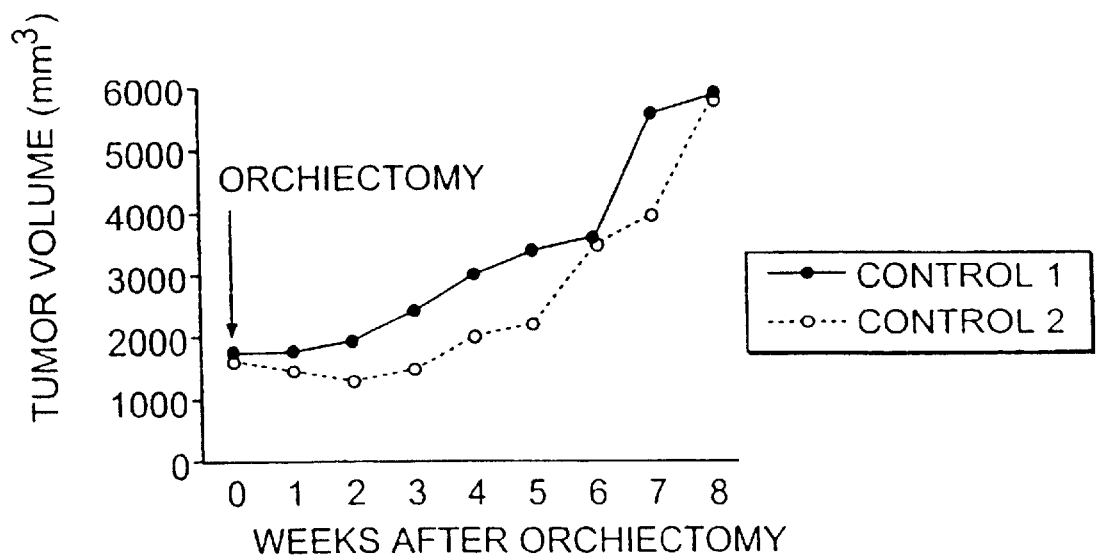
Figure 16A:
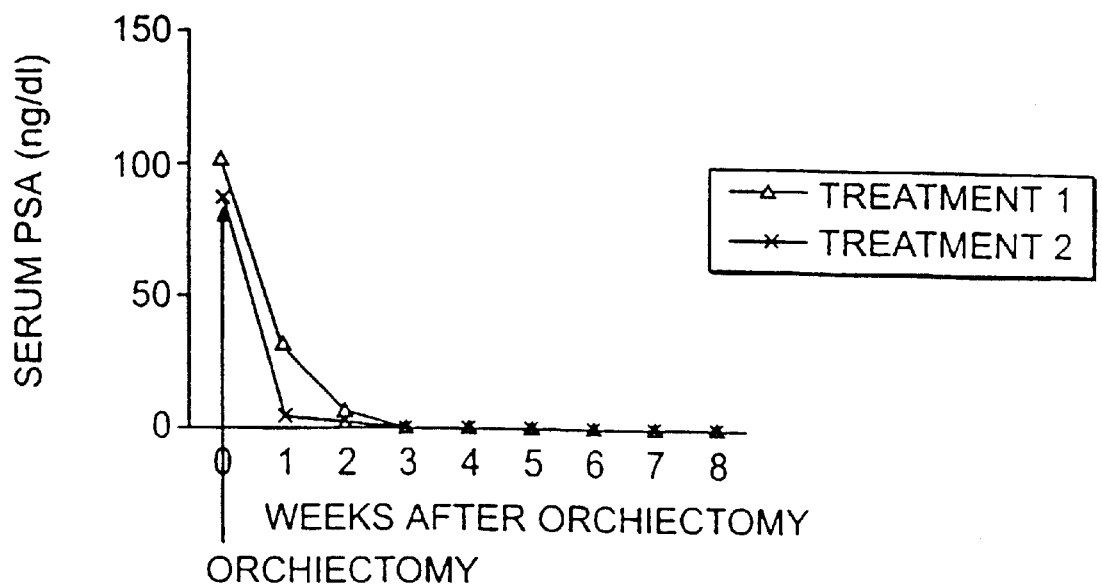
FIGS. 16a and 16b illustrate the effect of squalamine on PSA levels (a) and tumor growth (b) in athymic mice that underwent orchiectomy and subsequent treatment with squalamine.
Figure 16B:
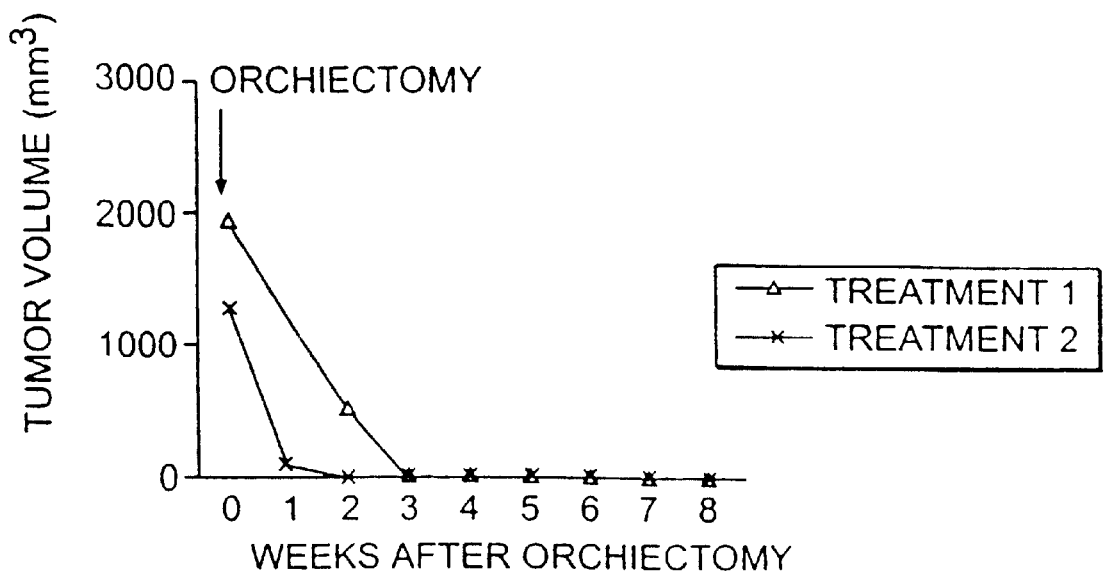

Ten mice began treatment with squalamine concomitant with the fall in PSA after castration (Group 1). Of these, three never experienced a post-orchiectomy PSA nadir, and one experienced an early death, of unknown etiology. Six animals, however, were treated with squalamine (at 20 mg/kg/day) for a range of six to ten weeks. These animals began squalamine treatment at the time of castration, or during the fall in PSA post-orchiectomy. All of these animals experienced a post-orchiectomy PSA nadir of less than I ng/dI, and maintained this negligible level for the duration of squalamine therapy. Tumor masses tended to diminish and, eventually, disappear, contrary to the response in control animals. The serum PSA levels and tumor volume measurements from two representational members of Group 1 are illustrated in FIGS. 16a and b, respectively. The response of animals that were treated with squalamine after the emergence of PSA rebound (Groups 2–4) was similar to the control, non-squalamine heated cohort, (FIG. 15) and is, therefore, not graphed.

EXAMPLE 7

Squalamine activity in combination with hormonal ablation

Human androgen dependent LNCaP cells ($2 \times 10_6$ cells/flank in both flanks) were implanted subcutaneously with an equal volume of Matrigel™ in forty athymic mice. These animals were followed with periodic bleedings until serum human PSA levels exceeded 100 ng/mL and tumor volume measurements exceeded 1000 mm$^3$ (approximately six weeks after implantation). All animals were then surgically castrated and were randomized into five treatment groups with 8–10 animals per group. One group of animals was not treated further (controls), while a second group immediately began daily intraperitoneal injection of 20 mg/kg/day squalamine (five days per week with a two day respite). A third group of animals began to receive squalamine (20 mg/kg/day squalamine, five days per week with a two day respite) when their serum human PSA levels reached values of 4–10 ng/mL. A fourth group of mice began squalamine treatment (20 mg/kg/day squalamine, five days per week with a two day respite)when serum human PSA values reached 20–40 ng/mL, and a fifth group began squalamine treatment when serum human PSA levels reached 100 ng/mL.

It was found that the human tumor xenografts responded to castration by a slowing or cessation of tumor growth following castration for 2–4 weeks before the tumors began growing again. Similarly, the serum human PSA levels fell to undetectable levels with a nadir at two weeks after castration, but by week three the serum human PSA levels began to rise in all control animals. For animals that were treated with squalamine after the emergence of PSA rebound, their response was similar to that of the control, non-squalamine treated animal cohort. For animals treated with squalamine concomitant with the fall in human PSA after castration, six of ten animals were treated for 6–10 weeks. Three mice in this group never experienced a post-orchiectomy PSA nadir, and one mouse experienced an early death of unknown etiology. The remaining six animals in this group experienced a post-orchiectomy PSA nadir of less than 1 ng/mL and maintained this negligible level for the duration of squalamine therapy. Tumor masses diminish with time and, eventually disappeared in all six animals.

Tissue histology was carried out on the tumor masses (or the site of tumor implantation, in the instance of the animals which underwent successful squalamine treatment) to examine the distribution of integrins in these tissues. One notable finding was that successful squalamine treatment coincided with observation of a reduction in the expression of the integrin $\alpha_v\beta_3$ and an increase in the integrin $\alpha_6\beta_4$ The integrin $\alpha_v\beta_3$ has been associated with a greater propensity for increased angiogenesis in tumors and for a tumor to grow and metastasize (e.g., cf. B. P. Eliceiri and D. A. Cheresh, *J. Clin. Invest.* 103, 1227–1230 (1999)). Thus, part of the mechanism by which squalamine successfully alters LNCaP tumor growth is by interfering with cellular integrin expression that is associated with tumor aggressiveness.

In vitro experiments were also conducted with the LNCAP cell line in which cell proliferation as judged by [3H]-thymidine uptake was determined. LNCaP cells were maintained as previously described (cf. J. T. Hsieh et al., *Cancer Research* 53, 2852–2857 (1993)). Cells were exposed to 20 ng/mL vascular endothelial growth factor (VEGF), 20 µg/mL squalamine or a combination of VEGF and squalamine. It was found that VEGF or squalamine alone had minimal effects on cell growth in media containing serum, but that the combination of VEGF and squalamine after 24 hours of exposure reduced [3H]-thymidine uptake by greater than 98% (Table 6). As a consequence, the mechanism underlying the effectiveness of squalamine treatment of the LNCaP tumor in vivo may under certain conditions also involve direct inhibition of tumor cell growth and/or induction of tumor cell death.

TABLE 6

| Endothelial Cell Treatment | Percent of Control [3H]-Thymidine Uptake |
| --- | --- |
| None (controls) | 100% |
| 20 ng/mL VEGF | 84% |
| 20 µg/mL squalamine | 75% |
| 20 ng/mL VEGF plus 20 µg/mL squalamine | <2% |

EXAMPLE 8

Squalamine activity in combination with carboplatin

About $5 \times 10^6$ cells from each of two human lung tumor lines, H460 (a rapidly proliferating large cell carcinoma cell line, ATCC HTB-177) and Calu-6 (an anaplastic carcinoma, ATCC HTB-56), were inoculated subcutaneously in the right foreleg of nude BALBc mice. Once tumors were visible (3–5 days) with a mean volume of approximately 50–80 mm$^3$, mice were treated intraperitoneally with 60 mg/kg carboplatin (single dose) or 20 mg/kg/squalamine (once daily for 5 days) or a combination of carboplatin and squalamine. There were 8 mice per group. Tumor growth inhibition was scored by quantifying the size of tumors once control tumors reached a size of 1.0 gram and determining the ratio of mean treated tumor size to mean control tumor size (T/C). Tumor growth inhibition was then scored as 100% x [1-(T/C)]. A separate antitumor activity variable, tumor growth delay, was scored for the tumors by determining the length of time it required for the mean tumor size in a treatment group to reach a size of 500 mm$^3$ (B. A. Teicher et al., *Anticancer Research* 18, 2567–2574 (1998)). The tumor growth inhibition seen with carboplatin plus squalamine was greater than that seen with carboplatin or squalamine alone. The relative inactivity of squalamine as a single agent by this assay endpoint supports the idea that squalamine is synergistic with carboplatin in the inhibition of these two human lung tumor xenografts. Similarly, it was determined that squalamine enhanced the tumor growth delay caused by carboplatin by an enhancement factor of >2.3 (Table 7).

TABLE 7

| Human lung tumor type: | H460 | Calu-6 |
|---|---|---|
| Tumor Growth Inhibition (T/C): | | |
| Carboplatin | 50% | 23% |
| Squalamine | 6% | 8% |
| Carboplatin + Squalamine | 77% | 52% |
| Tumor Growth Delay: | | |
| Carboplatin (C) | 2.9 | 2.5 |
| Carboplatin + Squalamine (© + S) | >6.7 | >6.3 |
| Enhancement Ratio, (© + S)/C | >2.3 | >2.5 |

EXAMPLE 9

In vivo Evaluation of squalamine activity in combination with carboplatin plus paclitaxel Female Sprague Dawley nu/nu mice weighing approximately 20 grams were implanted subcutaneously by trocar with fragments of MV-522 human lung tumors harvested from subcutaneously grown tumors in nude mice hosts. When tumors reached approximately 5×5 mm the animals were pair-matched into treatment and control groups. Each group contained 10 mice bearing tumors, was followed individually throughout the experiment. The administration of drugs (squalamine, paclitaxel plus carboplatin, or squalamine with paclitaxel and carboplatin) or vehicle began the day the animals were pair-matched (Day 1). Drug doses and schedule were selected based upon prior measurements of maximum tolerated doses for paclitaxel plus carboplatin in mice. Intraperitoneal (i.p.) dosing of drugs was selected as an acceptable surrogate for intravenous dosing.

Mice were weighed twice weekly, and tumor measurements were taken by calipers twice weekly, starting on Day 1. These tumor measurements were converted to mg tumor weight by the well-known formula, $L^2 \times 2 W$=tumor weight. The experiments were terminated when control tumors reached an estimated mean tumor size of one gram based upon in vivo tumor measurements. Upon termination, all mice were weighed, sacrificed, and their tumors excised. Excised tumors were weighed prior to their fixation in 10% formalin, and the mean excised tumor weight increase from Day 1 values for each treatment group was calculated for all animals surviving until the scheduled terminal sacrifice. In this xenograft model, the [mean excised treated tumor weight increase divided by the mean excised control tumor weight increase (T/C)]×100% was subtracted from 100% to give the tumor growth inhibition (TGI) value for each group. Mice with a reduction in tumor size at the end of the experiment relative to the initial tumor size were not included in the calculation of TGI and consequently TGI values may represent minimal estimates of tumor response to chemotherapy.

Some drug combinations caused shrinkage of some tumors in the MV-522 tumor xenograft model. With these combinations, the final weight of a given tumor (Day 31) was subtracted from its own calculated weight at the start of treatment on Day 1 for the relevant mice. This difference divided by the initial tumor weight times 100% was the percent shrinkage. A mean percent tumor shrinkage was then calculated from the data if more than one mouse in a group experienced a reduction in tumor size.

A tumor was considered to have experienced a partial regression if the reduction in tumor size was >50% at any time during the study. If the tumor completely disappeared in a mouse, this was considered a complete response or complete tumor shrinkage, which was then confirmed by histologic examination.

A one-way analysis of variance (ANOVA) with subsequent pairwise comparisons by Bonferroni's or Tukey's t-test was used for statistical analysis of excised tumor weight changes (R. R. Sokal and F. J. Rohlf, *Biometry*, W. H. Freeman and Company, San Francisco (1981); D. G. Altman, Practical Statistics for Medical Research, Chapman and Hall, New York (1991)). Homogeneity of variances was assessed using Levene's test and data with heterogeneous variances were log transformed appropriately before applying ANOVA. Data are presented as means ±S.E.M. or as percent of vehicle control. Nonparametric analyses of tumor weights that had non-normal distributions (determined by Kolmogorov-Smimov test) and/or unequal variances were also carried out using a Kruskal-Wallis statistical test, with Mann-Whitney rank sum test for pairwise comparisons. Differences between means or ranks as appropriate were considered significant when yielding a p-value $\geq 0.05$. P-values for squalamine containing regimens are calculated relative to the same regimen without squalamine.

Preliminary experiments confirmed that the use of paclitaxel at 10 mg/kg, qd×5, given i.p. in combination with carboplatin at 20 mg/kg, qd×5, given i.p. was tolerable to nude mice and represented the maximal combination dosing that was not toxic. The combination of paclitaxel and carboplatin at these doses and with this dosing regimen in the in vivo MV-522 human lung tumor xenograft model produced a mean excised tumor size of 365.9 ±66.0 mg at Day 31 or a TGI of 60.3% (p<0.01), with no evident tumor shrinkage for any animals in this treatment group. By contrast, triple combination chemotherapy with squalamine, paclitaxel and carboplatin produced a mean excised tumor growth of −0.1 ±19.3 mg (p<0.001) or a net tumor stasis for the triple therapy combination group of animals, despite no chemotherapy during the last three weeks prior to terminal sacrifice.

The TGI index for the squalamine/paclitaxel/carboplatin arm of this study was 96.1%. The benefit of chemotherapy on tumor size became apparent by Day 7 and differences in mean tumor sizes between the two paclitaxel and carboplatin-containing arms of this study increased thereafter. Tumors in the squalamine-treated animals scored at terminal sacrifice were significantly smaller than those seen in animals which received only paclitaxel and carboplatin. No mice receiving only paclitaxel and carboplatin were noted to undergo tumor shrinkage as assessed at the end of the experiment, but four mice in the triple combination chemotherapy cohort displayed tumor shrinkage over the course of the experiment, with a mean reduction in tumor size for these animals of 54.8%. There were no complete tumor regressions in any treatment group receiving paclitaxel/carboplatin and/or squalamine, and only in the triple combination chemotherapy group were there partial regressions (6 of 7 surviving animals). The transient reduction in tumor sizes was maximal on Day 14 of chemotherapy, as was seen with squalamine plus cisplatin.

The initial selection of squalamine dose and dosing regimen for combination chemotherapy was based on previous experiences with the maximum tolerated daily dose of squalamine and squalamine pharmacokinetics in rodents. Possible maintenance of squalamine activity with paclitaxel plus carboplatin at lower squalamine doses was separately investigated. A dose ranging experiment with the MV-522 lung tumor xenograft model was undertaken with paclitaxel and carboplatin using squalamine at daily doses of 0.2–20 mg/kg on Days 1–5 and 8–9. This experiment was terminated on Day 32 and final excised tumor weights and percent TGI values were determined, with mean values calculated on the basis of these observations (Table 7). At terminal sacrifice, mean excised control tumor growth was 674.3±75.8 mg, while the excised tumor growth in animals treated with paclitaxel and carboplatin alone was 223.4±82.5 mg. This corresponded to a TGI for paclitaxel plus carboplatin of 66.9%, which is similar to the 60.3% TGI seen in the first experiment for this double drug treatment (see above). The mean excised tumor growth values for squalamine-treated groups were 132.0±46.4 mg (TGI =74.2%) at a daily squalamine dose of 0.2 mg/kg (p>0.05) and less than 77.0 mg (TGI >78.8%) at 2.0, 10.0 and 20.0 mg/kg/day squalamine (Table 7). The maximal enhancement seen with multiple daily doses of squalamine occurred with 2.0 mg/kg/day dosing; at this dose, mean excised tumor growth was 22.9±25.0 mg, corresponding to a TGI of 92.1% (p=0.017). Statistically significant results were only observed at doses of 2.0 (p=0.017) and 10.0 (p=0.035) mg/kg/day squalamine and were not observed at 20 mg/kg/day (p>0.05) squalamine. However, a meta-analysis across this experiment and the previous one does show 20 mg/kg/day squalamine significantly enhances the effect of paclitaxel plus carboplatin (p<0.001). The advantage of adding squalamine to paclitaxel and carboplatin treatment of the MV-522 tumor was apparent at all doses by Day 5 and persisted throughout the course of the experiment.

No mice receiving paclitaxel and carboplatin alone had tumor shrinkages, but there were at lease two mice in each squalamine-treated group whose tumors were reduced in size over the course of the experiment, with a maximum of 5 mice out of 10 displaying tumor shrinkage at Day 32 in each of the groups receiving 2 or 10 mg/kg/day squalamine. No mice were observed with complete tumor shrinkages in any treatment group, but significant partial tumor regressions were seen in all treatment groups (including paclitaxel/carboplatin alone) which were most evident at Day 15 following initiation of chemotherapy. In the two squalamine treated groups with the greatest tumor response (2 and 10 mg/kg/day squalamine), 19 of 20 mice had a reduction in tumor burden of at least 50% at Day 15. The persistence of squalamine's effect on tumor growth in combination with paclitaxel and carboplatin more than three weeks after the last dosing with squalamine led to an investigation of the required period of time over which a squalamine dose was given that is important. A separate arm of the experiment described in the previous paragraph studied tumor growth for animal groups given squalamine b.i.d. as a single daily dose of 0.2–40 mg/kg with paclitaxel and carboplatin. There was a squalamine dose-related enhancement of tumor growth inhibition of paclitaxel and carboplatin for a single daily dose of squalamine. The best responses were seen at single daily squalamine doses of 10 and 20 mg/kg. At these doses, the mean excised tumor growths were 113.1 mg at 10 mg/kg and 96.6 mg at 20 mg/kg squalamine by Day 32, values which comparably favorably to mean excised tumor values of 674.3 mg for control tumors and 223.4 mg for paclitaxel and carboplatin-treated tumors. However, no squalamine dose achieved statistical significance when compared to paclitaxel and carboplatin alone. Partial tumor regressions were seen in 2–4 squalamine-treated mice during the experiment and durable partial tumor shrinkages were seen in 2–3 animals in each squalamine-treated group when they were evaluated at the end of the experiment, but no reduction in tumor size was seen with any mice treated with paclitaxel and carboplatin alone. There also was one complete regression observed in a mouse which received 20 mg/kg squalamine on day 5 along with paclitaxel and carboplatin. The mean percent tumor shrinkages in the squalamine-treated animals with tumor regressions was in the range of 21.0–50.4%.

EXAMPLE 10

Squalamine activity in combination with radiation therapy

Syngeneic mammary carcinoma MCA-4 tumor cells ($5\times10^5$) were injected intramuscularly into the right legs of C3Hf/Kam male mice (4 months of age). When the tumors reached 6 mm in diameter, the mice were randomly assigned to receive: (a) no treatment, (b) squalamine alone (20 mg/kg/day b.i.d. for 11–14 days), (c) 15 Gy of gamma irradiation, or (d) squalamine plus 15 Gy of gamma rays. Tumor growth was followed until tumors reached at least 12 mm in diameter. The effect of squalamine on tumor radio-response was determined by absolute and normalized tumor growth delays (AGD and NGD). AGD is defined as the time in days for tumors treated with radiation (or squalamine) to grow from 8 to 12 mm minus the time in days for untreated tumors to grow from 8–12 mm. NGD is defined as the time in days for tumors treated with both squalamine and radiation to grow from 8 to 12 mm minus the time in days for tumors treated with squalamine only to grow from 8 to 12 mm. An enhancement factor (EF) was determined as the ratio of NGD to AGD. The EF for squalamine with 15 Gy gamma rays calculated from the observed times for tumor growth (Table 8) is >1.5.

TABLE 8

| Treatment Condition | Time to Grow From 8 to 12 mm (days) | AGD (in days) | NGD (in days) |
| --- | --- | --- | --- |
| None (controls) | 6 | | |
| 15 Gy gamma rays | 18 | 12 | |
| Squalamine | 6 | 0 | |
| 15 Gy + Squalamine | >24 | | >18 |

EXAMPLE 11

Squalamine activity in combination with cisplatin for ovarian cancer

Human ovarian tumor cells were injected subcutaneously ($5 \times 10^7$ cells per animal) in the mid-back region of female Swiss nude mice. The human ovarian tumors were either the parental 2008 cell line (cf. R. J. Pietras et al., *Oncogene* 9, 1829–1838 (1994)) or a transfected variant overexpressing the Her-2/neu receptor. The overexpression of the Her-2/neu receptor is considered to make the resulting xenograft tumors more angiogenic and less responsive to chemotherapy. After one week, animals were randomized to groups receiving no treatment (controls), a single dose of cisplatin (4 mg/kg), daily treatment with squalamine (2 mg/kg, days 1–10) or cisplatin plus squalamine. The growth of tumors was then scored on day 28 following initiation of chemotherapy. The results were very similar with the parental 2008 tumor and the transfected variant overexpressing the Her-2/neu receptor. Exemplary results with the parental 2008 cell line are shown in Table 9. These results can be quantified by calculating a tumor growth inhibition index for each treatment group. In this xenograft model, the [day 28 mean treated tumor weight increase divided by the day 28 mean control tumor weight increase (T/C)] x 100% was subtracted from 100% to give the tumor growth inhibition (TGI) value for each group. Cisplatin had minimal effect on 2008 tumor cell growth in this model, but squalamine significantly reduced day 28 mean tumor size compared to controls. The combination of cisplatin plus squalamine was highly effective at slowing tumor growth.

TABLE 9

| Treatment Condition | Day 28 Mean Tumor Size (mm³) | Tumor Growth Inhibition (TGI) Index (%) |
| --- | --- | --- |
| None (controls) | 6197 | |
| Cisplatin | 5108 | 18% |
| Squalamine | 2254 | 41% |
| Cisplatin plus squalamine | 356 | 94% |

We claim:

1. A method for treating a tumor that is sensitive to squalamine, comprising the step of: exposing the tumor to an effective dosage of radiation in a first treatment procedure; and administering an effective amount of squalamine in a second treatment procedure and wherein the effective amount is a synergistically effective amount.

2. A method according to claim 1, wherein in the second treatment procedure, the squalamine is administered subcutaneously.

3. A method according to claim 1, wherein in the second treatment procedure, the squalamine is administered orally.

4. A method according to claim 1, wherein in the second treatment procedure, the squalamine is administered intravenously.

5. A method according to claim 1, wherein in the second treatment procedure, the squalamine is administered intraperitoneally.

6. A method according to claim 1, wherein the tumor is a CNS tumor.

7. A method according to claim 1, wherein the tumor is a breast tumor.

8. A method according to claim 1, wherein the tumor is a lung tumor.

9. A method according to claim 1, wherein the tumor is an ovarian tumor.

10. A method according to claim 1, wherein the tumor is a prostate tumor.

11. A method according to claim 1, wherein the tumor is a neuroblastoma.

12. A method according to any one of claims 1, wherein the first and second treatments are administered simultaneously or are administered as a single composition.

13. A method according to claim 1, wherein said radiation is gamma radiation.

14. A method according to claim 1, wherein said radiation is x-ray radiation.

* * * * *